US006844317B2

(12) United States Patent
Winslow et al.

(10) Patent No.: US 6,844,317 B2
(45) Date of Patent: Jan. 18, 2005

(54) METHODS FOR OXYGEN TRANSPORT COMPRISING A HIGH OXYGEN AFFINITY MODIFIED HEMOGLOBIN

(75) Inventors: Robert M. Winslow, La Jolla, CA (US); Kim D. Vandegriff, San Diego, CA (US)

(73) Assignee: Sangart, Inc., San Diego, CA (US)

( * ) Notice: Subject to any disclaimer, the term of this patent is extended or adjusted under 35 U.S.C. 154(b) by 47 days.

(21) Appl. No.: 10/340,141

(22) Filed: Jan. 10, 2003

(65) Prior Publication Data

US 2003/0162693 A1 Aug. 28, 2003

Related U.S. Application Data

(63) Continuation-in-part of application No. 10/114,400, filed on Apr. 1, 2002.
(60) Provisional application No. 60/347,741, filed on Jan. 11, 2002.

(51) Int. Cl.[7] ............................................. A61K 38/00
(52) U.S. Cl. ........................................................ 514/6
(58) Field of Search ............................... 514/6; 424/177

(56) References Cited

U.S. PATENT DOCUMENTS

| | | | |
|---|---|---|---|
| 3,518,982 A | 7/1970 | Timmins et al. ................ 128/2 |
| 3,925,344 A | 12/1975 | Mazur ..................... 260/112.5 |
| 3,956,259 A | 5/1976 | Garcia et al. ................ 260/112 |
| 4,001,200 A | 1/1977 | Bonsen et al. ........... 260/112.5 |
| 4,001,401 A | 1/1977 | Bonson et al. .............. 424/177 |
| 4,053,590 A | 10/1977 | Bonsen et al. .............. 424/177 |
| 4,061,736 A | 12/1977 | Morris et al. ............... 424/177 |
| 4,064,118 A | 12/1977 | Wong ............................ 514/6 |
| 4,113,853 A | 9/1978 | Funakoshi et al. ............. 514/6 |
| 4,133,874 A | 1/1979 | Miller et al. .................. 424/38 |
| 4,179,337 A | 12/1979 | Davis et al. ................. 435/181 |
| 4,209,300 A | 6/1980 | Thibault ....................... 23/230 |
| 4,301,144 A | 11/1981 | Iwashita et al. ............... 424/78 |
| 4,336,248 A | 6/1982 | Bonhard et al. ............. 424/101 |
| 4,377,512 A | 3/1983 | Ajisaka et al. .............. 260/112 |
| 4,401,652 A | 8/1983 | Simmonds et al. ......... 424/101 |
| 4,412,989 A | 11/1983 | Iwashita et al. ............ 424/177 |
| 4,439,357 A | 3/1984 | Bonhard et al. ............ 260/112 |
| 4,473,494 A | 9/1984 | Tye ............................ 260/112 |
| 4,473,496 A | 9/1984 | Scannon ................ 260/112 B |
| 4,526,715 A | 7/1985 | Kothe et al. ................ 260/112 |
| 4,529,719 A | 7/1985 | Tye ................................ 514/6 |
| 4,532,130 A | 7/1985 | Djordjevich et al. ........ 424/101 |
| 4,584,130 A | 4/1986 | Bucci et al. ............ 260/112 B |
| 4,598,064 A | 7/1986 | Walder ........................... 514/6 |
| 4,600,531 A | 7/1986 | Walder ........................ 530/385 |
| 4,650,786 A | 3/1987 | Wong ............................ 514/6 |
| 4,670,417 A | 6/1987 | Iwasaki et al. ................. 514/6 |
| 4,710,488 A | 12/1987 | Wong ............................ 514/6 |
| 4,738,952 A | 4/1988 | Ecanow et al. ................ 514/6 |
| 4,777,244 A | 10/1988 | Bonhard et al. ............ 530/385 |
| 4,826,811 A | 5/1989 | Sehgal et al. .................. 514/6 |
| 4,831,012 A | 5/1989 | Estep ............................ 514/6 |
| 4,857,636 A | 8/1989 | Hsia ............................ 530/385 |
| 4,861,867 A | 8/1989 | Estep .......................... 530/385 |
| 4,900,780 A | 2/1990 | Cerny ........................ 525/54.1 |
| 4,911,929 A | 3/1990 | Farmer et al. ............... 424/450 |
| 4,920,194 A | 4/1990 | Filler et al. ................. 530/385 |
| 4,987,154 A | 1/1991 | Long, Jr. ..................... 514/772 |
| 5,028,588 A | 7/1991 | Hoffman et al. ............... 514/6 |
| 5,041,615 A | 8/1991 | Hai et al. .................... 560/143 |
| 5,058,416 A | 10/1991 | Engelhardt et al. ........ 73/19.01 |
| 5,061,688 A | 10/1991 | Beissinger et al. ............ 514/6 |
| 5,077,036 A | 12/1991 | Long, Jr. ....................... 424/5 |
| 5,080,885 A | 1/1992 | Long, Jr. ....................... 424/5 |
| 5,084,558 A | 1/1992 | Rausch et al. .............. 530/385 |
| 5,114,932 A | 5/1992 | Runge ......................... 514/58 |
| 5,115,100 A | 5/1992 | Wu et al. ..................... 530/385 |
| 5,128,452 A | 7/1992 | Hai et al. .................... 530/385 |
| 5,194,590 A | 3/1993 | Sehgal et al. ............... 530/385 |
| 5,200,323 A | 4/1993 | Chang et al. ................ 435/7.1 |
| 5,217,648 A | 6/1993 | Beissinger et al. ......... 252/314 |
| 5,234,903 A | 8/1993 | Nho et al. ..................... 514/6 |
| 5,239,061 A | 8/1993 | Fronticelli et al. .......... 530/385 |
| 5,248,766 A | 9/1993 | Nelson et al. .............. 530/385 |
| 5,250,665 A | 10/1993 | Kluger et al. ................ 530/52 |
| 5,264,555 A | 11/1993 | Shorr et al. ................. 530/385 |
| 5,281,579 A | 1/1994 | Estep ............................ 514/6 |
| 5,295,944 A | 3/1994 | Teicher et al. ................. 600/1 |

(List continued on next page.)

FOREIGN PATENT DOCUMENTS

| | | |
|---|---|---|
| DE | 2430898 | 1/1976 |
| EP | 0340908 | 4/1989 |
| EP | 0361719 | 4/1990 |
| EP | 0478048 | 4/1992 |
| JP | 02124445 | 5/1990 |
| WO | WO 87/07832 | 12/1987 |
| WO | WO 90/13309 | 11/1990 |
| WO | WO 91/07190 | 5/1991 |

OTHER PUBLICATIONS

Bouwer et al, "Diffusiion Coefficients of Oxygen and Hemoglobin Measured by Facilitated Oxygen Diffusion Through Hemoglobin Solutions", *Biochim et Biophys Acta*, 1338:127–136 (1997).

Chien, "Rhenology in the Microcirculation in Normal and Low Flow States", *Advances in Shock Research* 80:71–80 (1982).

Frank et al, "A Finite–Element Model of Oxygen Diffusion in the Pulmonary Capillaries", *J Appl Physiol:* 2036–2044 (1997).

(List continued on next page.)

*Primary Examiner*—Christopher R. Tate
*Assistant Examiner*—Maury Audet
(74) *Attorney, Agent, or Firm*—Burns, Doane, Swecker & Mathis LLP

(57) ABSTRACT

The present invention relates to blood products, and more particularly to compositions comprising a modified oxygenated hemoglobin having a high affinity for oxygen and methods for making such compositions. Such compositions according to the present invention have better stability to autooxidation and superior oxygen carrying characteristics.

43 Claims, 10 Drawing Sheets

U.S. PATENT DOCUMENTS

| | | | |
|---|---|---|---|
| 5,296,465 A | 3/1994 | Rausch et al. | 514/6 |
| 5,312,808 A | 5/1994 | Shorr et al. | 514/6 |
| 5,334,705 A | 8/1994 | Bonaventura et al. | 530/385 |
| 5,334,706 A | 8/1994 | Przybelski | 530/385 |
| 5,344,393 A | 9/1994 | Roth et al. | 604/4 |
| 5,349,054 A | 9/1994 | Bonaventura et al. | 530/385 |
| 5,352,773 A | 10/1994 | Kandler et al. | 530/385 |
| 5,386,014 A | 1/1995 | Nho et al. | 530/385 |
| 5,407,428 A | 4/1995 | Segall et al. | 604/28 |
| 5,438,041 A | 8/1995 | Zheng et al. | 514/6 |
| 5,439,591 A | 8/1995 | Pliura et al. | 210/635 |
| 5,449,759 A | 9/1995 | Hoffman et al. | 530/385 |
| 5,451,205 A | 9/1995 | Roth et al. | 604/6 |
| 5,464,814 A | 11/1995 | Sehgal | 514/6 |
| 5,478,805 A | 12/1995 | Shorr et al. | 514/6 |
| 5,478,806 A | 12/1995 | Nho | 514/6 |
| 5,480,866 A | 1/1996 | Bonaventura et al. | 514/6 |
| 5,510,464 A | 4/1996 | Przybelski | 530/385 |
| 5,525,630 A | 6/1996 | Hoffman | 514/563 |
| 5,532,352 A | 7/1996 | Pliura et al. | 540/145 |
| 5,545,328 A | 8/1996 | Pliura et al. | 210/635 |
| 5,545,727 A * | 8/1996 | Hoffman et al. | 536/23.4 |
| 5,554,638 A | 9/1996 | Dewhirst et al. | 514/398 |
| 5,563,254 A | 10/1996 | Hoffman et al. | 536/23.5 |
| 5,571,801 A | 11/1996 | Segall et al. | 514/59 |
| 5,574,019 A | 11/1996 | Segall et al. | 514/23 |
| 5,578,564 A | 11/1996 | Chivers et al. | 514/6 |
| 5,585,484 A * | 12/1996 | Acharya et al. | 540/145 |
| 5,591,710 A | 1/1997 | Hsia | 514/6 |
| 5,595,723 A | 1/1997 | Quay | 424/9.5 |
| 5,599,907 A | 2/1997 | Anderson et al. | 530/385 |
| 5,612,310 A * | 3/1997 | Dewhirst et al. | 514/6 |
| 5,613,944 A | 3/1997 | Segall et al. | 604/28 |
| 5,614,490 A | 3/1997 | Przybelski | 514/6 |
| 5,618,919 A | 4/1997 | Rausch et al. | 530/385 |
| 5,628,930 A | 5/1997 | Weers et al. | 252/312 |
| 5,631,219 A | 5/1997 | Rosenthal et al. | 514/6 |
| 5,635,538 A | 6/1997 | Weers et al. | 514/743 |
| 5,635,539 A | 6/1997 | Clark, Jr. et al. | 514/759 |
| 5,650,388 A | 7/1997 | Shorr et al. | 514/6 |
| 5,661,124 A | 8/1997 | Hoffman et al. | 514/6 |
| 5,814,601 A * | 9/1998 | Winslow et al. | 514/6 |
| 5,985,825 A | 11/1999 | Winslow et al. | 514/6 |
| 6,054,427 A * | 4/2000 | Winslow | 514/6 |
| 6,269,679 B1 | 8/2001 | McCarthy et al. | 73/19.1 |
| 6,432,918 B1 * | 8/2002 | Winslow | 514/6 |

OTHER PUBLICATIONS

Frazier, O. H., Myocardial Revascularization with Laser—Preliminary Findings, Circulation, 1995; 92 [suppl II;II–58–II–65].

Hellums et al, "Simulation of Intraluminal Gas Transport Processes in the Microcirculation", *Annals of Biomed Engineering* 24:1–24 (1996).

Intaglietta et al, "Microvascular and Tissue Oxygen Distribution", *Cardiovasc Research* 32:632–643 (1996).

Intaglietta, "Whiaker Lecture 1996: Microcirculation, Biomedical Engineering, and Artificial Blood", *Ann Biomed Engineer* 25:593–603 (1997).

Juszczak et al., "UV Resonance Raman Study of β93–Modified Hemoglobin A: Chemical Modifier–Specific Effects and Added Influences of Attached Poly(ethylene glycol) Chains", *Biochemistry* 41:376–385 (2002).

Kerger et al., "Systemic and Subcutaneous Micrivascular Oxygen Tension in Conscious Syrian Golden Hamsters",*Am J Physiol* 267 (*Heart Circ. Physiol.* 37):H802–810 (1995).

Kim et al, "Oxygen Tension Regulates the Nitric Oxide Pathway", *J Clin Invest* 91:437–442 (1993).

Mirhashemi et al., "Model Analysis Of The Enhancement Of Tissue Oxygenation By Hemodilution Due To Increased Microvascular Flow Velocity", *Microvasc Res* 34:290–301 (1987).

Mirhashemi et al., "Effects Of Hemodilution On Skin Microcirculation", *Am J Physiol* 254:H411–H416 (1988).

Nishide et al., "Facilitated Oxygen Transport with Modified And Encapsulated Hemoglobins Across Non–Flowing Solution Membrane", *Art. Cells, Blood Su.b., and Immo.b Biotech.* 25(4):335–346 (1997).

"Oxygen Diffuses from Arterioles to Capillaries", *NIPS* 224 (1990).

Papenfuss et al., "A Transparent Access Chamber for the Rat Dorsal Skin Fold", *Microvase Res* 18:311–318 (1979).

Popel, Invited Editorial on "A Finite–Element Model of Oxygen Diffusion in the Pulmonary Capillaries", *J Appl Physiol:* 17171718 (1997).

Prouchayret et al., "A Potential Blood Substitute From Carboxyl Dextran And Oxyhemoglobin", I. Preparation, Purification and Characterization, *Biomat Art Cells & Immob Biotech* 20:319–322 (1992).

Reinhart et al., "Rheologic Measurements on Small Samples with a New Capillary viscosimeter", *J Lab Clin Med* 104:921–931 (1984).

Stetter et al., "Influence Of Recombinant Hemoglobin Solution On Blood Rheology", *Transfusion* 37:1149–1155 (1977).

Tsai and Intaglietta, "Local Tissue Oxygenation By Statistically Distributed Sources", *Microvasc Res* 44:200–213 (1992).

Tsai et al., "Microcirculatory Consequences Of Blood Substitution With αα–Hemoglobin", in Winslow et al., (eds)., *Blood Substitutes. Physiological Basis of Efficacy,* Birkhauser, Boston. Mass. pp. 155–174 (1995).

Wittenberg, "Myoglobin–Facilitated Oxygen Diffusion: Role of Myoglobin in Oxygen Entry into Muscle", *Physiological Reviews* 50 (4):559–636 (1970).

Prough et al. "Effects of Hypertonic Saline Versus Ringer's Solution on Cerebral Oxygen Transport During Resuscitation from Hemorrhagic Shock" J. Neurosurg. 64:627–32 (1986).

Przybelski et al. "The Pressor Effect of Hemoglobin—Good or Bad?" In *Advances in Blood Substitutes, Industrial Opportunities and Medical Challenges* (Winslow et al., Eds.) Boston, Birkhäuser pp. 71–85 (1997).

Rohlfs et al. "Arterial Blood Pressure Responses to Cell–free Hemoglobin Solutions and the Reaction with Nitric Oxide" J. Biol. Chem. 273:12128–12134 (1998).

Rowe. "Probing Hydration and the Stability of Protein Solutions—A Colloid Science Approach" Biophysical Chemistry 93:93–101 (2001).

Sakai et al. "Changes in Resistance Vessels During Hemorrhagic Shock and Resuscitation in Conscious Hamster Model" Am. J. Physiol. 276(45):H563–H571 (1999).

Sakai et al. "Molecular Dimensions of Hb–Based $O_2$ Carriers Determine Constriction of Resistance Arteries and Hypertension" Am J. Physiol. 279:H908–H915 (2000).

Springer et al. "Discrimination Between Oxygen and Carbon Monoxide and Inhibition of Autooxidation by Myoglobin" Journal of Biological Chemistry 264(6):3057–3060.

Vandegriff et al. "Hemoglobin–Oxygen Equilibrium Binding: Rapid–Scanning Spectrophotometry and Singular Value Decomposition" Methods in Enzymology 232:460–485 (1994).

Vandegriff. "Stability and Toxicity of Hemoglobin Solutions" Chapter 8 In *Blood Substitutes: Physiological Basis of Efficacy* (Winslow et al., Eds.) Birkhäuser Boston pp. 105–131 (1995).

Vandegriff et al. "Colloid Osmotic Properties of Modified Hemoglobins: Chemically Cross–linked Versus Polyethylene Glycol Surface–conjugated" Biophys Chem 69:23–30 (1997).

Vandegriff et al. "Colloid Osmotic Effects of Hemoglobin–Based Oxygen Carriers" In *Advances in Blood Substitutes Industrial Opportunities and Medical Challenges* (Winslow et al. Eds.) Boston, Birkhäuser pp. 207–232 (1997).

Vandegriff et al. "Hemoglobinoxygen Equilibrium Cures Measured During Enzymatic Oxygen Consumption" Anal. Biochem. 256:107–116 (1998).

Winslow et al. "Oxygen Equilibrium Curve of Normal Human Blood and Its Evaluation by Adair's Equation" J. Biol. Chem. 252 (7):2331–37 (1977).

Winslow. "A Model for Red Cell $O_2$ Uptake" Int J Clin Monit Comput 2:81–93 (1985).

Winslow et al. "Hemoglobin Oxygen Affinity and the Design of Red Cell Substitutes" In *Advances in Blood Substitutes* (Birkhauser, Ed.) Boston, Mass. pp. 167–188 (1997).

Winslow et al. "Vascular Resistance and the Efficacy of Red Cell Substitutes in Rat Hemorrhage Model" J. Appl. Physiol. 85:993–1003 (1998).

Winslow. "αα–Crosslinked Hemoglobin: Was Failure Predicted by Preclinical Testing?" Vox Sang 79:1–20 (2000).

* cited by examiner

FPLC chromatogram of MalPEG-Hb and SFH

Oxygen equilibrium curves for SFH and MalPEG-Hb

METHODS FOR OXYGEN TRANSPORT COMPRISING A HIGH OXYGEN AFFINITY MODIFIED HEMOGLOBIN

CROSS-REFERENCE TO RELATED APPLICATIONS

This application is a continuation-in-part of copending U.S. Ser. No. 10/114,400, filed Apr. 1, 2002 and claims priority under 35 U.S.C. §119(e) to U.S. Ser. No. 60/347,741, filed Jan. 11, 2002.

TECHNICAL FIELD

The present invention relates to blood products, and more particularly to compositions comprising a modified hemoglobin having a high affinity for oxygen and methods for making such compositions.

BACKGROUND OF THE INVENTION

The Circulatory System and the Nature of Hemoglobin

The blood is the means for delivering nutrients to the tissues and removing waste products from the tissues for excretion. The blood is composed of plasma in which red blood cells (RBCs or erythrocytes), white blood cells (WBCs), and platelets are suspended. Red blood cells comprise approximately 99% of the cells in blood, and their principal function is the transport of oxygen to the tissues and the removal of carbon dioxide therefrom.

The left ventricle of the heart pumps the blood through the arteries and the smaller arterioles of the circulatory system. The blood then enters the capillaries, where the majority of the exchange of nutrients and cellular waste products occurs. (See, e.g., A. C. Guyton, "Human Physiology And Mechanisms Of Disease" (3rd. ed.; W. B. Saunders Co., Philadelphia, Pa.), pp. 228–229 (1982)). Thereafter, the blood travels through the venules and veins in its return to the right atrium of the heart. Though the blood that returns to the heart is oxygen-poor compared to that which is pumped from the heart, when at rest, the returning blood still contains about 75% of the original oxygen content.

The reversible oxygenation function (i.e., the delivery of oxygen) of RBCs is carried out by the protein hemoglobin. In mammals, hemoglobin has a molecular weight of approximately 64,000 daltons and is composed of about 6% heme and 94% globin. In its native form, it contains two pairs of subunits (i.e., it is a tetramer), each containing a heme group and a globin polypeptide chain. In aqueous solution, hemoglobin is present in equilibrium between the tetrameric (MW 64,000) and dimeric forms (MW 32,000); outside of the RBC, the dimers are prematurely excreted by the kidney (plasma half-life of approximately 2–4 hours). Along with hemoglobin, RBCs contain stroma (the RBC membrane), which comprises proteins, cholesterol, and phospholipids.

Exogenous Blood Products

Due to the demand for blood products in hospitals and other settings, extensive research has been directed at the development of blood substitutes and plasma expanders. A blood substitute is a blood product that is capable of carrying and supplying oxygen to the tissues. Blood substitutes have a number of uses, including replacing blood lost during surgical procedures and following acute hemorrhage, and for resuscitation procedures following traumatic injury. Plasma expanders are blood substitutes that are administered into the vascular system but are typically not capable of carrying oxygen. Plasma expanders can be used, for example, for replacing plasma lost from burns, to treat volume deficiency shock, and to effect hemodilution (e.g., for the maintenance of normovolemia and to lower blood viscosity). Essentially, blood substitutes can be used for these purposes or any purpose in which banked blood is currently administered to patients. (See, e.g., U.S. Pat. Nos. 4,001,401 to Bonson et al., and 4,061,736 to Morris et al.)

The current human blood supply is associated with several limitations that can be alleviated through the use of an exogenous blood substitute. To illustrate, the widespread availability of safe and effective blood substitutes would reduce the need for banked (allogeneic) blood. Moreover, such blood substitutes would allow the immediate infusion of a resuscitation solution following traumatic injury without regard to cross-matching (as is required for blood), thereby saving valuable time in resupplying oxygen to ischemic tissue. Likewise, blood substitutes can be administered to patients prior to surgery, allowing removal of autologous blood from the patients which could be returned later in the procedure, if needed, or after surgery. Thus, the use of exogenous blood products not only protects patients from exposure to non-autologous (allogeneic) blood, it conserves either autologous or allogeneic (banked, crossmatched) blood for its optimal use.

Limitations of Current Blood Substitutes

Attempts to produce blood substitutes (sometimes referred to as "oxygen-carrying plasma expanders") have thus far produced products with marginal efficacy or whose manufacture is tedious, expensive, or both. Frequently, the cost of manufacturing such products is so high that it effectively precludes the widespread use of the products, particularly in those markets where the greatest need exists (e.g., emerging third-world economies).

Blood substitutes can be grouped into the following three categories: i) perfluorocarbon-based emulsions, ii) liposome-encapsulated hemoglobin, and iii) modified cell-free hemoglobin. As discussed below, none has been entirely successful, though products comprising modified cell-free hemoglobin are thought to be the most promising. Perfluorochemical-based compositions dissolve oxygen as opposed to binding it as a ligand. In order to be used in biological systems, the perfluorochemical must be emulsified with a lipid, typically egg-yolk phospholipid. Though the perfluorocarbon emulsions are inexpensive to manufacture, they do not carry sufficient oxygen at clinically tolerated doses to be effective. Conversely, while liposome-encapsulated hemoglobin has been shown to be effective, it is far too costly for widespread use. (See generally, Winslow, Robert M., "Hemoglobin-based Red Cell Substitutes," Johns Hopkins University Press, Baltimore (1992)).

Most of the blood substitute products in clinical trials today are based on modified hemoglobin. These products, frequently referred to as hemoglobin-based oxygen carriers (HBOCs), generally comprise a homogeneous aqueous solution of a chemically-modified hemoglobin, essentially free from other red cell residue (stroma). Although stroma-free hemoglobin (SFH) from humans is the most common raw material for preparing a HBOC, other sources of hemoglobin have also been used. For example, hemoglobin can be obtained or derived from animal blood (e.g., bovine or porcine hemoglobin) or from bacteria or yeast or transgenic animals or plants molecularly altered to produce a desired hemoglobin product.

The chemical modification is generally one of intramolecular cross-linking, oligomerization and/or polymer conjugation to modify the hemoglobin such that its persistence in the circulation is prolonged relative to that of unmodified hemoglobin, and its oxygen binding properties are similar to those of blood. Intramolecular cross-linking chemically binds together subunits of the tetrameric hemoglobin unit to prevent the formation of dimers which, as previously indicated, are prematurely excreted. (See, e.g., U.S. Pat. No. 5,296,465 to Rausch et al.)

The high costs of manufacturing HBOC products have greatly limited their commercial viability. In addition, the present inventors have found that known HBOCs have a tendency to release excessive amounts of oxygen to the tissues at the arteriole walls rather than the capillaries. This can result in insufficient oxygen available for delivery by the HBOC to the tissues surrounding the capillaries. This is despite the fact that the initial loading of the HBOC with oxygen may be relatively high, compared with that normally achieved with natural red blood cells, except in the case of very low affinity mutants.

In most instances, HBOCs have been designed to have oxygen affinities that are the same as or lower than that of native hemoglobin. However, as discussed above, this may result in insufficient delivery of oxygen to the tissues. Accordingly, the present invention relates to a blood substitute that comprises an HBOC with high oxygen affinities in an aqueous diluent.

SUMMARY OF THE INVENTION

The methods and compositions of the present invention are useful in a variety of settings including emergency rooms, operating rooms, military conflicts, cancer hospitals, and veterinary clinics. The low toxicity and high stability of the present invention permits storage at room temperature without compromising the efficacy of the described blood substitute. The present invention also circumvents the requirement for blood-type cross-matching and the associated laboratory testing, allowing for earlier and safer intervention in patient treatment. The combination of low toxicity, long-term stability, and universal applicability of the present invention therefore presents a particularly useful substitute for blood.

In one aspect, the present invention provides a blood substitute product comprising surface-modified oxygenated hemoglobin, wherein the surface-modified oxygenated hemoglobin has a P50 less than native stroma-free hemoglobin from the same animal source (i.e. from the same species of animal) when measured under the same conditions. Suitable animal sources include, e.g., humans, cows, pigs, horses.

In a preferred embodiment, the blood substitute product takes the form of a composition comprising the surface-modified oxygenated hemoglobin and an aqueous diluent.

In a specific embodiment, the surface-modified oxygenated hemoglobin has a P50 less than 10 torr, preferably less than 7 torr.

In another aspect, the present invention provides a blood substitute product produced by covalently attaching one or more polyalkylene oxides to the oxygenated hemoglobin.

In a specific embodiment, the blood substitute product is produced by covalently attaching a polymer of a polyalkylene oxide such as polyethylene glycol (PEG) having the formula $H(OCH_2CH_2)_nOH$, where n is greater than or equal to 4. Preferably, the product has a methemoglobin/total hemoglobin ratio less than 0.10.

In yet another aspect, the present invention provides a blood substitute product stable to autooxidation at 24° C., comprising a PEG-hemoglobin conjugate, wherein the methemoglobin/total hemoglobin ratio is less than 0.10 and the PEG-hemoglobin conjugate has a P50 less than 10 torr.

In another aspect, the present invention provides a method of making a blood substitute composition comprising the steps of: a) preparing hemoglobin having a methemoglobin/total hemoglobin ratio less than 0.10; b) covalently attaching polyalkylene oxide to the hemoglobin to form surface-modified oxygenated hemoglobin having a P50 less than 10 torr; and c) suspending the surface-modified oxygenated hemoglobin in a suitable diluent. Preferably preparing hemoglobin further comprises isolating hemoglobin from red blood cells.

In addition, the step of preparing the hemoglobin can further comprise isolating hemoglobin from red blood cells, wherein the hemoglobin has a methemoglobin/total hemoglobin ratio of 0.10 or greater, and exposing the hemoglobin to aerobic conditions (i.e. to the atmosphere) for a time sufficient to lower the methemoglobin/total hemoglobin ratio to less than 0.10. This step may be carried out in the absence of a thiol-containing reducing agent.

In yet another aspect, the present invention provides a method of using a blood substitute product to deliver oxygen to a tissue, comprising administering the product in an aqueous diluent to a mammal in need thereof.

Other aspects of the present invention are described throughout the specification.

DESCRIPTION OF THE INVENTION

Figure 1:
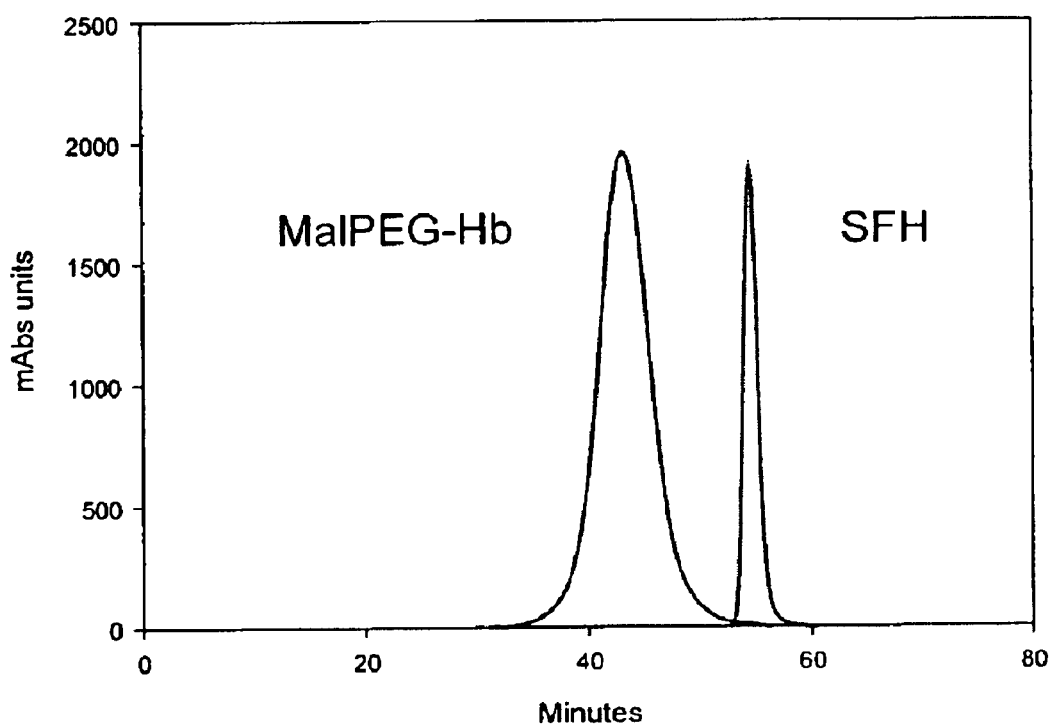
FIG. 1 depicts the FPLC chromatogram of MalPEG-Hb and SFH.

The present invention is directed to blood substitutes comprising HBOCs having high oxygen affinity. For certain applications, these compositions are capable of delivering oxygen to tissues more efficiently than blood substitutes with oxygen affinities that approximate native hemoglobin.

Definitions

To facilitate understanding of the invention set forth in the disclosure that follows, a number of terms are defined below.

The term "hemoglobin" refers generally to the protein contained within red blood cells that transports oxygen. Each molecule of hemoglobin has 4 subunits, 2 α chains and 2 β chains, which are arranged in a tetrameric structure. Each subunit also contains one heme group, which is the iron-containing center that binds oxygen. Thus, each hemoglobin molecule can bind 4 oxygen molecules.

The term "modified hemoglobin" includes, but is not limited to, hemoglobin altered by a chemical reaction such as intra- and inter-molecular cross-linking, genetic manipulation, polymerization, and/or conjugation to other chemical groups (e.g., polyalkylene oxides, for example polyethylene glycol, or other adducts such as proteins, peptides, carbohydrates, synthetic polymers and the like). In essence, hemoglobin is "modified" if any of its structural or functional properties have been altered from its native state. As used herein, the term "hemoglobin" by itself refers both to native, unmodified, hemoglobin, as well as modified hemoglobin.

The term "surface-modified hemoglobin" is used to refer to hemoglobin described above to which chemical groups such as dextran or polyalkylene oxide have been attached, most usually covalently. The term "surface modified oxygenated hemoglobin" refers to hemoglobin that is in the "R" state when it is surface modified.

The term "stroma-free hemoglobin" refers to hemoglobin from which all red blood cell membranes have been removed.

The term "methemoglobin" refers to an oxidized form of hemoglobin that contains iron in the ferric state and cannot function as an oxygen carrier.

The term "MalPEG-Hb" refers to hemoglobin to which malemidyl-activated PEG has been conjugated. Such MalPEG may be further referred to by the following formula:

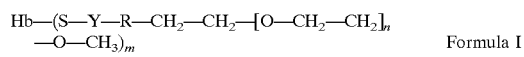

Formula I where Hb refers to tetrameric hemoglobin, S is a surface thiol group, Y is the succinimido covalent link between Hb and Mal-PEG, R is an alkyl, amide, carbamate or phenyl group (depending on the source of raw material and the method of chemical synthesis), $[O-CH_2-CH_2]_n$ are the oxyethylene units making up the backbone of the PEG polymer, where n defines the length of the polymer (e.g., MW=5000), and $O-CH_3$ is the terminal methoxy group. PHP and POE are two different PEG-modified hemoglobin.

The term "perfluorocarbons" refers to synthetic, inert, molecules that contain fluorine atoms, and that consist entirely of halogen (Br, F, Cl) and carbon atoms. In the form of emulsions, they are under development as blood substances, because they have the ability to dissolve many times more oxygen than equivalent amounts of plasma or water.

The term "plasma expander" refers to any solution that may be given to a subject to treat blood loss.

The term "oxygen carrying capacity," or simply "oxygen capacity" refers to the capacity of a blood substitute to carry oxygen, but does not necessarily correlate with the efficiency in which it delivers oxygen. Oxygen carrying capacity is generally calculated from hemoglobin concentration, since it is known that each gram of hemoglobin binds 1.34 ml of oxygen. Thus, the hemoglobin concentration in g/dl multiplied by the factor 1.34 yields the oxygen capacity in ml/dl. Hemoglobin concentration can be measured by any known method, such as by using the β-Hemoglobin Photometer (HemoCue, Inc., Angelholm, Sweden). Similarly, oxygen capacity can be measured by the amount of oxygen released from a sample of hemoglobin or blood by using, for example, a fuel cell instrument (e.g., Lex-$O_2$-Con; Lexington Instruments).

The term "oxygen affinity" refers to the avidity with which an oxygen carrier such as hemoglobin binds molecular oxygen. This characteristic is defined by the oxygen equilibrium curve which relates the degree of saturation of hemoglobin molecules with oxygen (Y axis) with the partial pressure of oxygen (X axis). The position of this curve is denoted by the value, P50, the partial pressure of oxygen at which the oxygen carrier is half-saturated with oxygen, and is inversely related to oxygen affinity. Hence the lower the P50, the higher the oxygen affinity. The oxygen affinity of whole blood (and components of whole blood such as red blood cells and hemoglobin) can be measured by a variety of methods known in the art. (See, e.g., Winslow et al., *J. Biol. Chem.* 252(7):2331–37 (1977)). Oxygen affinity may also be determined using a commercially available HEMOX™ TM Analyzer (TCS Scientific Corporation, New Hope, Pa.). (See, e.g., Vandegriff and Shrager in "Methods in Enzymology" (Everse et al., eds.) 232:460 (1994)).

The terms "hypertonic" means a colloidal solution with a colloidal osmotic pressure (oncotic) than blood (>approximately 25–27 mm Hg). Colloid osmotic pressure may be measured by any suitable technique, such as in a Wescor instrument.

The term "oxygen-carrying component" refers broadly to a substance capable of carrying oxygen in the body's circulatory system and delivering at least a portion of that oxygen to the tissues. In preferred embodiments, the oxygen-carrying component is native or modified hemoglobin, and is also referred to herein as a "hemoglobin based oxygen carrier," or "HBOC".

The term "hemodynamic parameters" refers broadly to measurements indicative of blood pressure, flow and volume status, including measurements such as blood pressure, cardiac output, right atrial pressure, and left ventricular end diastolic pressure.

The term "crystalloid" refers to small molecules (usually less than 10 Å) such as salts, sugars, and buffers. Unlike colloids, crystalloids do not contain any oncotically active components and equilibrate in between the circulation and interstitial spaces very quickly.

The term "colloid," in contrast to "crystalloid" refers to larger molecules (usually greater than 10 Å) that equilabrate across biological membranes depending on their size and charge and includes proteins such as albumin and gelatin, as well as starches such as pentastarch and hetastarch.

The term "colloid osmotic pressure" refers to the pressure exerted by a colloid to equilibrate fluid balance across a membrane.

The term "stable to autooxidation" refers to the ability of a HBOC to maintain a low rate of autoxidation. HBOC is considered stable at 24° C. if the methemoglobin/total hemoglobin ratio does not increase more than 2% after 10 hours at 24° C. For example, if the rate of autoxidation is 0.2 $hr^{-1}$, then if the initial percentage of methemoglobin is 5%, HBOC would be considered stable at room temperature for 10 hours if this percentage did not increase above 7%.

The term "methemoglobin/total hemoglobin ratio" refers to the ratio of deoxygenated hemoglobin to total hemoglobin.

The term "mixture" refers to a mingling together of two or more substances without the occurrence of a reaction by which they would lose their individual properties; the term "solution" refers to a liquid mixture; the term "aqueous solution" refers to a solution that contains some water and may also contain one or more other liquid substances with water to form a multi-component solution; the term "approximately" refers to the actual value being within a range, e.g. 10%, of the indicated value.

The term "polyethylene glycol" refers to liquid or solid polymers of the general chemical formula $H(OCH_2CH_2)_n OH$, where n is greater than or equal to 4. Any PEG formulation, substituted or unsubstituted, can be used.

The meaning of other terminology used herein should be easily understood by someone of reasonable skill in the art.

The Nature of Oxygen Delivery and Consumption

Although the successful use of the compositions and methods of the present invention do not require comprehension of the underlying mechanisms of oxygen delivery and consumption, basic knowledge regarding some of these putative mechanisms may assist in understanding the discussion that follows. It has generally been assumed that the capillaries are the primary conveyors of oxygen to the tissue. However, regarding tissue at rest, current findings indicate that there is approximately an equipartition between arteriolar and capillary oxygen release. That is, hemoglobin in the arterial system is believed to deliver approximately one third of its oxygen content in the arteriolar network and one-third in the capillaries, while the remainder exits the microcirculation via the venous system.

The arteries themselves are sites of oxygen utilization. For example, the artery wall requires energy to effect regulation of blood flow through contraction against vascular resistance. Thus, the arterial wall is normally a significant site for the diffusion of oxygen out of the blood. However, current oxygen-delivering compositions (e.g., HBOCs) may release too much of their oxygen content in the arterial system, and thereby induce an autoregulatory reduction in capillary perfusion. Accordingly, the efficiency of oxygen delivery of a blood substitute may actually be hampered by having too much oxygen or too low an oxygen affinity.

The rate of oxygen consumption by the vascular wall, i.e., the combination of oxygen required for mechanical work and oxygen required for biochemical synthesis, can be determined by measuring the gradient at the vessel wall. See, e.g., Winslow, et al., in "Advances in Blood Substitutes" (1997), Birkhauser, ed., Boston, Mass., pages 167–188. Present technology allows accurate oxygen partial pressure measurements in a variety of vessels. The measured gradient is directly proportional to the rate of oxygen utilization by the tissue in the region of the measurement. Such measurements show that the vessel wall has a baseline oxygen utilization which increases with increases in inflammation and constriction, and is lowered by relaxation.

The vessel wall gradient is inversely proportional to tissue oxygenation. Vasoconstriction increases the oxygen gradient (tissue metabolism), while vasodilation lowers the gradient. Higher gradients are indicative of the fact that more oxygen is used by the vessel wall, while less oxygen is available for the tissue. The same phenomenon is believed to be present throughout the microcirculation.

The Relationship Between Vasoconstriction and Oxygen Affinity

The rationale for developing an HBOC with high oxygen affinity is based, in part, on past studies using cell-free hemoglobins as alternatives to red blood cell transfusions. Some of the physiological effects of these solutions remain incompletely understood. Of these, perhaps the most controversial is the propensity to cause vasoconstriction, which may be manifest as hypertension in animals and man (Amberson, W., "Clinical experience with hemoglobin-saline solutions,". Science 106: 117–117 (1947)) (Keipert, P., A. Gonzales, C. Gomez, V. Macdonald, J. Hess, and R. Winslow, "Acute changes in systemic blood pressure and urine output of conscious rats following exchange transfusion with diaspirin-crosslinked hemoglobin solution," Transfusion 33: 701–708, (1993)). Human hemoglobin crosslinked between α chains with bis-dibromosalicyl-fumarate (ααHb) was developed by the U.S. Army as a model red cell substitute, but was abandoned by the Army after demonstration of severe increases in pulmonary and systemic vascular resistance (Hess, J., V. Macdonald, A. Murray, V. Coppes, and C. Gomez, "Pulmonary and systemic hypertension after hemoglobin administration" Blood 78: 356A (1991)). A commercial version of this product was also abandoned after a disappointing Phase III clinical trial (Winslow, R. M. "αα-Crosslinked hemoglobin: Was failure predicted by preclinical testing?" Vox sang 79: 1–20 (2000).

The most commonly advanced explanation for the vasoconstriction produced by cell-free hemoglobin is that it readily binds the endothelium-derived relaxing factor, nitric oxide (NO). In fact, recombinant hemoglobins with reduced affinity for NO have been produced which appear to be less hypertensive in top-load rat experiments (Doherty, D. H., M. P. Doyle, S. R. Curry, R. J. Vali, T. J. Fattor, J. S. Olson, and D. D. Lemon, "Rate of reaction with nitric oxide determines the hypertensive effect of cell-free hemoglobin," Nature Biotechnology 16: 672–676 (1998)) (Lemon, D. D., D. H. Doherty, S. R. Curry, A. J. Mathews, M. P. Doyle, T. J. Fattor, and J. S. Olson, "Control of the nitric oxide-scavenging activity of hemoglobin," Art Cells, Blood Subs., and Immob. Biotech 24: 378 (1996)). However, studies suggest that NO binding may not be the only explanation for the vasoactivity of hemoglobin. It has been found that certain large hemoglobin molecules, such as those modified with polyethylene glycol (PEG), were virtually free of the hypertensive effect, even though their NO binding rates were identical to those of the severely hypertensive ααHb (Rohlfs, R. J., E. Bruner, A. Chiu, A. Gonzales, M. L. Gonzales, D. Magde, M. D. Magde, K. D. Vandegriff, and R. M. Winslow, "Arterial blood pressure responses to cell-free hemoglobin solutions and the reaction with nitric oxide," J Biol Chem 273: 12128–12134 (1998)). Furthermore, it was found that PEG-hemoglobin was extraordinarily effective in preventing the consequences of hemorrhage when given as an exchange transfusion prior to hemorrhage (Winslow, R. M., A. Gonzales, M. Gonzales, M. Magde, M. McCarthy, R. J. Rohlfs, and K. D. Vandegriff, "Vascular resistance and the efficacy of red cell substitutes," J Appl Physiol 85: 993–1003 (1998)).

This protective effect correlated with the lack of hypertension, suggesting that vasoconstriction is responsible for the disappointing performance of many of the hemoglobin-based products studied to date. Based on these observations, a hypothesis was developed to explain vasoconstriction, as an alternative, or possibly in addition to, the effect of NO binding. Although not wishing to be bound by any particular theory, it is believed that a substantial component of hemoglobin's vasoactive effect is a reflexive response to the diffusion of hemoglobin in the cell-free space. This hypothesis was tested in an in vitro capillary system, and it was demonstrated that PEG-hemoglobin, which has a reduced diffusion constant, transferred $O_2$ in a manner very similar to that of native red blood cells (McCarthy, M. R., K. D. Vandegriff, and R. M. Winslow, "The role of facilitated diffusion in oxygen transport by cell-free hemoglobin: Implications for the design of hemoglobin-based oxygen carriers," *Biophysical Chemistry* 92: 103–117 (2001)). Oxygen affinity would be expected to play a role in its facilitated diffusion by hemoglobin in the plasma space, since the change in saturation from the hemoglobin to the vessel wall is a determinant of the diffusion gradient of the hemoglobin itself.

Oxygen affinity of cell-free hemoglobin may play an additional role in the regulation of vascular tone, since the release of $O_2$ to vessel walls in the arterioles will trigger vasoconstriction (Lindbom, L., R. Tuma, and K. Arfors, "Influence of oxygen on perfusion capillary density and capillary red cell velocity in rabbit skeletal muscle," *Microvasc Res* 19: 197–208 (1980)). In the hamster skinfold, the $PO_2$ in such vessels is in the range of 20–40 Torr, where the normal red cell oxygen equilibrium curve is steepest (Intaglietta, M., P. Johnson, and R. Winslow, "Microvascular and tissue oxygen distribution," *Cardiovasc Res* 32: 632–643 (1996)). Thus from a theoretical point of view, it may be important for the P50 of cell-free hemoglobin to be lower than that of red cells (i.e., higher $O_2$ affinity), in order to prevent release of $O_2$ in arteriolar regulatory vessels.

Oxygen-Carrying Component

In preferred embodiments, the oxygen carrier (i.e., the oxygen-carrying component) is a hemoglobin-based oxygen carrier, or HBOC. The hemoglobin may be either native (unmodified); subsequently modified by a chemical reaction such as intra- or inter-molecular cross-linking, polymerization, or the addition of chemical groups (e.g., polyalkylene oxides, or other adducts); or it may be recombinantly engineered. Human alpha- and beta-globin genes have both been cloned and sequenced. Liebhaber, et al., P.N.A.S. 77: 7054–7058 (1980); Marotta, et al., J. Biol. Chem. 353: 5040–5053 (1977) (beta-globin cDNA). In addition, many recombinantly produced modified hemoglobins have now been produced using site-directed mutagenesis, although these "mutant" hemoglobin varieties were reported to have undesirably high oxygen affinities. See, e.g., Nagai, et al., P.N.A.S., 82: 7252–7255 (1985).

The present invention is not limited by the source of the hemoglobin. For example, the hemoglobin may be derived from animals and humans. Preferred sources of hemoglobin for certain applications are humans, cows and pigs. In addition, hemoglobin may be produced by other methods, including chemical synthesis and recombinant techniques. The hemoglobin can be added to the blood product composition in free form, or it may be encapsulated in a vessicle, such as a synthetic particle, microballoon or liposome. The preferred oxygen-carrying components of the present invention should be stroma free and endotoxin free. Representative examples of oxygen-carrying components are disclosed in a number of issued United States Patents, including U.S. Pat. No. 4,857,636 to Hsia; U.S. Pat. No. 4,600,531 to Walder, U.S. Pat. No. 4,061,736 to Morris et al.; U.S. Pat. No. 3,925,344 to Mazur; U.S. Pat. No. 4,529,719 to Tye; U.S. Pat. No. 4,473,496 to Scannon; U.S. Pat. No. 4,584,130 to Bocci et al.; U.S. Pat. No. 5,250,665 to Kluger et al.; U.S. Pat. No. 5,028,588 to Hoffman et al.; and U.S. Pat. No. 4,826,811 and U.S. Pat. No. 5,194,590 to Sehgal et al.

In addition to the aforementioned sources of hemoglobin, it has recently been found that horse hemoglobin has certain advantages as the oxygen carrying component in the compositions of the present invention. One advantage is that commercial quantities of horse blood are readily available from which horse hemoglobin can be purified. Another unexpected advantage is that horse hemoglobin exhibits chemical properties that may enhance its usefulness in the blood substitutes of the present invention.

Previous reports have indicated that horse hemoglobin auto-oxidizes to methemoglobin faster than human hemoglobin, which would make it less desirable as a blood substitute component. See, e.g., J. G. McLean and I. M. Lewis, Research in Vet. Sci., 19:259–262 (1975). In order to minimize auto-oxidation, McLean and Lewis used a reducing agent, glutathione, after red blood cell lysis. However, the hemoglobin that is used to prepare the compositions of the present invention, regardless of whether the source of hemoglobin is human or horse, do not require the use of reducing agents to prevent auto-oxidation after red blood cell lysis.

More recently, it has been reported that horse hemoglobin has an oxygen affinity that is different from that of human hemoglobin. See, e.g., M. Mellegrini, et al., Eur. J. Biochem., 268: 3313–3320 (2001). Such a difference would discourage the selection of horse hemoglobin to prepare blood substitutes that mimic human hemoglobin. However, when incorporated into the compositions of the present invention, no significant difference (less than 10%) in oxygen affinity between human and horse hemoglobin-containing conjugates is observed.

Accordingly, contrary to these seemingly undesirable properties, in the compositions of the present invention, horse hemoglobin is equivalent if not superior to human hemoglobin.

For use in the present invention, the HBOC has an oxygen affinity that is greater than whole blood, and preferably twice that of whole blood, or alternatively, greater than that of stroma-free hemoglobin (SFH), when measured under the same conditions. In most instances, this means that the HBOC in the blood substitute will have a P50 less than 10, and more preferably less than 7. In the free state, SFH has a P50 of approximately 15 torr, whereas the P50 for whole blood is approximately 28 torr. It has previously been suggested that increasing oxygen affinity, and thereby lowering the P50, may enhance delivery of oxygen to tissues, although it was implied that a P50 lower than that of SFH would not be acceptable. See Winslow, et al., in "Advances in Blood Substitutes" (1997), Birkhauser, ed., Boston, Mass., at page 167, and U.S. Pat. No. 6,054,427. This suggestion contradicts the widely held belief that modified hemoglobins for use as blood substitutes should have lower oxygen affinities, and should have P50s that approximate that of whole blood. Hence, many researchers have used pyridoxyl phosphate to raise the P50 of SFH from 10 to approximately 20–22, since pyridoxylated hemoglobin more readily releases oxygen when compared to SFH.

There are many different scientific approaches to manufacturing HBOCs with high oxygen affinity (i.e. those with P50s less than SFH). For example, studies have identified the amino acid residues that play a role in oxygen affinity, such as B-93 Cysteine, and thus site-directed mutagenesis can now be easily carried out to manipulate oxygen affinity to the desired level. See, e.g., U.S. Pat. No. 5,661,124. Many other approaches are discussed in U.S. Pat. No. 6,054,427.

Hemoglobin-Associated Toxicity

Hemoglobin is known to exhibit autooxidation when it reversibly changes from the ferrous ($Fe^{2+}$) to the ferric ($Fe^{3+}$) or methemoglobin form. When this happens, molecular oxygen dissociates from the oxyhemoglobin in the form of a superoxide anion ($O_2^-$). This also results in destabilization of the heme-globin complex and eventual denaturation of the globin chains. Both oxygen radical formation and protein denaturation are believed to play a role in vivo toxicity of HBOCs (Vandegriff, K. D., Blood Substitutes, Physiological Basis of Efficacy, pages 105–130, Winslow et al., ed., Birkhauser, Boston, Mass. (1995).)

With most HBOCs, there is a negative correlation between oxygen affinity and hemoglobin oxidation, i.e., the higher the oxygen affinity, the lower the rate of autooxidation. However, the effects of different hemoglobin modifications on oxygen affinity and the rate of autooxidation are not always predictable. In addition, the optimal balance between oxygen affinity and autooxidation rate is not well understood.

The present invention relates, in part, to the unexpected finding that the PEG-Hb conjugates described herein exhibit very low rates of autooxidation. When measured as a rate of oxidation, this value should be as low as possible (i.e.,0.2% per hour of total hemoglobin, more preferably 0.1% per hour of total hemoglobin, at room temperature for at least 3 hours, and more preferably at least 10 hours. Thus, the HBOCs of the present invention remain stable during administration and/or storage at room temperature.

Modifications of the Oxygen-Carrying Component

In a preferred embodiment, the oxygen-carrying component is modified hemoglobin. A preferred modification to hemoglobin is "surface-modification," i.e. covalent attachment of chemical groups to the exposed amino acid side chains on the hemoglobin molecule.

Modification is carried out principally to increase the molecular size of the hemoglobin, most often by covalent attachment of polymeric moieities such as synthetic polymers, carbohydrates, proteins and the like. Generally, synthetic polymers are preferred.

Suitable synthetic hydrophilic polymers include, inter alia, polyalkylene oxide, such as polyethylene oxide $((CH_2CH_2O)_n)$, polypropylene oxide $((CH(CH_3)CH_2O)_n)$ or a polyethylene/polypropylene oxide copolymer $((CH_2CH_2O)_n—(CH(CH_3)CH_2O)_n)$. Other straight, branched chain and optionally substituted synthetic polymers that would be suitable in the practice of the present invention are well known in the medical field.

Most commonly, the chemical group attached to the hemoglobin is polyethylene glycol (PEG), because of its pharmaceutical acceptability and commercial availability. PEGs are polymers of the general chemical formula $H(OCH_2CH_2)_nOH$, where n is generally greater than or equal to 4. PEG formulations are usually followed by a number that corresponds to their average molecular weight. For example, PEG-200 has an average molecular weight of 200 and may have a molecular weight range of 190–210. PEGs are commercially available in a number of different forms, and in many instances come preactivated and ready to conjugate to proteins.

An important aspect of preferred embodiments of the present invention is that surface modification takes place when the hemoglobin is in the oxygenated or "R" state. This is easily accomplished by allowing the hemoglobin to equilibrate with the atmosphere (or, alternatively, active oxygenation can be carried out) prior to conjugation. By performing the conjugation to oxygenated hemoglobin, the oxygen affinity of the resultant hemoglobin is enhanced. Such a step is generally regarded as being contraindicated, since many researchers describe deoxygenation prior to conjugation to diminish oxygen affinity. See, e.g., U.S. Pat. No. 5,234,903.

Although in many respects the performance of surface modified hemoglobins is independent of the linkage between the hemoglobin and the modifier (e.g. PEG), it is believed that more rigid linkers such as unsaturated aliphatic or aromatic $C_1$ to $C_6$ linker substituents may enhance the manufacturing and/or characteristics of the conjugates when compared to those that have more flexible and thus deformable modes of attachment.

The number of PEGs to be added to the hemoglobin molecule may vary, depending on the size of the PEG. However, the molecular size of the resultant modified hemoglobin should be sufficiently large to avoid being cleared by the kidneys to achieve the desired half-life. Blumenstein, et al., determined that this size is achieved above 84,000 molecular weight. (Blumenstein, et al., in "Blood Substitutes and Plasma Expanders," Alan R. Liss, editors, New York, N.Y., pages 205–212 (1978).) Therein, the authors conjugated hemoglobin to dextran of varying molecular weight. They reported that a conjugate of hemoglobin (with a molecular weight of 64,000) and dextran (having a molecular weight of 20,000) "was cleared slowly from the circulation and negligibly through the kidneys," but increasing the molecular weight above 84,000 did not alter the clearance curves. Accordingly, as determined by Blumenstein, et al., it is preferable that the HBOC have a molecular weight of at least 84,000.

In one embodiment of the present invention, the HBOC is a "MalPEG," which stands for hemoglobin to which malemidyl-activated PEG has been conjugated. Such MalPEG may be further referred to by the following formula:

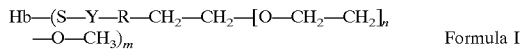

$$Hb—(S—Y—R—CH_2—CH_2—[O—CH_2—CH_2]_n—O—CH_3)_m \quad \text{Formula I}$$

where Hb refers to tetrameric hemoglobin, S is a surface thiol group, Y is the succinimido covalent link between Hb and Mal-PEG, R is an alkyl, amide, carbamate or phenyl group (depending on the source of raw material and the method of chemical synthesis), $[O—CH_2—CH_2]_n$ are the oxyethylene units making up the backbone of the PEG polymer, where n defines the length of the polymer (e.g., MW=5000), and $O—CH_3$ is the terminal methoxy group.

Crystalloid Component

In one embodiment of the present invention, the blood substitute may also comprise a crystalloid. The crystalloid component can be any crystalloid which, in the form of the blood substitute composition, is preferably capable of achieving an osmolarity greater than 800 mOsm/l, i.e. it makes the blood substitute "hypertonic". Examples of suitable crystalloids and their concentrations in the blood substitute include, e.g., 3% NaCl, 7% NaCl, 7.5% NaCl, and 7.5% NaCl in 6% dextran. More preferably, the blood substitute has an osmolarity of between 800 and 2400 mOsm/l. The use of recombinantly produced hemoglobins in solutions with an osmolality between 300–800 mOsm/l that further comprise a colloid (i.e. a molecule less diffusible than dextrose) have been previously reported. See, e.g., U.S. Pat. No. 5,661,124. However, this patent teaches away from producing blood substitutes with osmolalities above 800, and suggests that the hemoglobin concentration should be between 6–12 g/dl. In contrast, the oxygen carrying efficiency of compositions of the present invention permit lower concentrations of hemoglobin to be used, such as greater than 6 g/dl or even greater than 4 g/dl. When the blood substitute further comprises a crystalloid and is hypertonic, the compositions of present invention may provide improved functionality for rapid recovery of hemodynamic parameters over other blood substitute compositions, which include a colloid component. Small volume highly hypertonic crystalloid infusion (e.g., 1–10 ml/kg) provides significant benefits in the rapid and sustained recovery of acceptable hemodynamic parameters in controlled hemorrhage. (See, e.g., Przybelski, R. J., E. K. Daily, and M. L. Birnbaum, "The pressor effect of hemoglobin—good or bad?" In Winslow, R. M., K. D. Vandegriff, and M. Intaglietta, eds. Advances in Blood Substitutes. Industrial Opportunities and Medical Challenges. Boston, Birkhäuser (1997), 71–85). Hypertonic crystalloid solutions alone, however, do not adequately restore cerebral oxygen transport. See D. Prough, et al., "Effects of hypertonic saline versus Ringer's solution on cerebral oxygen transport during resuscitation from hemorrhagic shock," J. Neurosurg. 64:627–32 (1986).

Formulation

The blood substitutes of the present invention are formulated by mixing the oxygen carrier and other optional excipients with a suitable diluent. Although the concentration of the oxygen carrier in the diluent may vary according to the application, and in particular based on the expected post-administration dilution, in preferred embodiments, because of the other features of the compositions of the present invention that provide for enhanced oxygen delivery and therapeutic effects, it is usually unnecessary for the concentration to be above 6 g/dl, and is more preferably between 0.1 to 4 g/dl.

Suitable diluents (i.e., one which is pharmaceutically acceptable for intravenous injection) include, intra alia, proteins, glycoproteins, polysaccharides, and other colloids. It is not intended that these embodiments be limited to any particular diluent. Thus, it is intended that the diluent encompass aqueous cell-free solutions of albumin, other colloids, or other non-oxygen carrying components, and the aqueous solution has a viscosity of at least 2.5 cP. In some preferred embodiments, the viscosity of the aqueous solution is between 2.5 and 4 cP. It is contemplated that the present invention also encompasses solutions with a viscosity of 6 cP or greater.

Applications

A. Clinical Applications

It is contemplated that the present invention and its embodiments will be useful in applications where a rapid restoration of $O_2$ levels or an increased $O_2$ level or a replacement of $O_2$ levels is clinically indicated. See, e.g., U.S. Pat. No. 6,054,427. The numerous settings in which the methods and compositions of the present invention find use include the following:

Trauma. An acute loss of whole blood can result in a fluid shift from the interstitial and intracellular spaces to replace the lost volume of blood while shunting of blood away from the low priority organs including the skin and gut. Shunting of blood away from organs reduces and sometimes eliminates $O_2$ levels in these organs and results in progressive tissue death. Rapid restoration of $O_2$ levels is contemplated as perhaps resulting in a signficantly better salvage of tissues in patients suffering such acute blood loss.

Ischemia. In ischemia, a particular organ (or organs) are "starved" for oxygen. Small sections of the organ, known as infarcts, begin to die as a result of the lack of $O_2$. Rapid restoration of $O_2$ levels is critical is stemming infarct formation in critical tissues. Conditions resulting in ischemia include heart attack, stroke, or cerbrovascular trauma.

Hemodilution: In this clinical application, a blood substitute is required to replace blood that is removed pre-operatively. It is contemplated that the patient blood removal occurs to prevent a requirement for allogeneic transfusions post-operatively. In this application, the blood substitute is administered to replace (or substitute for) the $O_2$ levels of the removed autologous blood. This permits the use of the removed autologous blood for necessary transfusions during and after surgery. One such surgery requiring pre-operative blood removal would be a cardiopulmonary bypass procedure.

Septic Shock. In overwhelming sepsis, some patients may become hypertensive in spite of massive fluid therapy and treatment with vasocontrictor agents. In this instance, the overproduction of nitric oxide (NO) results in the lowered blood pressure. Therefore hemoglobin is close to an ideal agent for treatment of these patients because hemoglobin binds NO with an avidity that parallels $O_2$.

Cancer. Delivery of $O_2$ to the hypoxic inner core of a tumor mass increases its sensitivity to radiotherapy and chemotherapy. Because the microvasculature of a tumor is unlike that of other tissues, sensitization through increasing $O_2$ levels requires $O_2$ be unloaded within the hypoxic core. In other words, the P50 should be very low to prevent early unloading of the $O_2$, increasing the $O_2$ levels, to insure optimal sensitization of the tumor to subsepuent radiation and chemotherapy treatments.

Chronic anemia. In these patients, replacement of lost or metabolized hemoglobin is compromised or completely absent. It is contemplated that the blood substitute must effectively replace or increase the reduced $O_2$ levels in the patient.

Sickle cell anemia. In sickle cell anemia, the patient is debilitated by a loss of $O_2$ levels that occurs during the sickling process as well as a very high red blood cell turnover rate. The sickling process is a function of $PO_2$ where the lower the $PO_2$, the greater the sickling rate. It is contemplated that the ideal blood substitute would restore patient $O_2$ levels to within a normal range during a sickling crisis.

Cardioplegia. In certain cardiac surgical procedures, the heart is stopped by appropriate electrocyte solutions and reducing patient temperature. Reduction of the temperature will significantly reduce the P50, possibly preventing unloading of $O_2$ under any ordinary physiological conditions. Replacement of $O_2$ levels is contemplated as potentially reducing tissue damage and death during such procedures.

Hypoxia. Soldiers, altitude dwellers, and world-class athletes under extreme conditions may suffer reduced $O_2$ levels because extraction of $O_2$ from air in the lung is limited. The limited $O_2$ extraction further limits $O_2$ transport. It is contemplated that a blood substitute could replace or increase the $O_2$ levels in such individuals.

Organ Perfusion. During the time an organ is maintained ex vivo, maintaining $O_2$ content is essential to preserving structural and cellular intergrity and minimizing infarct formation. It is contemplated that a blood substitute would sustain the $O_2$ requirements for such an organ.

Cell Culture. This requirement is virtually identical to that of organ perfusion, except that the rate of $O_2$ consumption may be higher.

Hematopoiesis. It is contemplated that the blood substitute serves as a source for heme and iron for use in the synthesis of new hemoglobin during hematopoiesis.

B. Veterinary Applications

The present invention can also be used in non-humans. The methods and compositions of the present invention may be used with domestic animals such as livestock and companion animals (e.g, dogs, cats, horses, birds, reptiles), as well as other animals in aquaria, zoos, oceanaria, and other facilities that house animals. It is contemplated that the present invention finds utility in the emergency treatment of domestic and wild animals suffering a loss of blood due to injury, hemolytic anemias, etc. For example, it is contemplated that embodiments of the present invention are useful in conditions such as equine infectious anemia, feline infectious anemia, hemolytic anemia due to chemicals and other physical agents, bacterial infection, Factor IV fragmentation, hypersplenation and splenomegaly, hemorrhagic syndrome in poultry, hypoplastic anemia, aplastic anemia, idiopathic immune hemolytic conditions, iron deficiency, isoimmune hemolytic anemia, microangiopathic hemolytic, parasitism, etc. In particular, the present invention finds use in areas where blood donors for animals of rare and/or exotic species are difficult to find.

EXAMPLES

Example 1

Production of Stroma-Free Hemoglobin

Step-1—Procurement of Outdated Red Blood Cells

Outdated packed red blood cells are procured from a commercial source, such as the San Diego Blood Bank or the American Red Cross. Preferably, outdated material is received not more than 45 days from the time of collection. Packed RBCs (pRBCs) are stored at 4±2° C. until further processed (1–7 days). All units are screened for viral infection and subjected to nucleic acid testing prior to use.

Step-2—Pooling of Outdated Blood

Packed red blood cells are pooled into a sterile vessel in a clean facility. Packed red blood cell volume is noted, and hemoglobin concentration is determined using a commercially available co-oximeter or other art-recognized method.

Step-3—Leukodepletion

Leukodepletion (i.e. removal of white blood cells) is carried out using membrane filtration. Initial and final leukocyte counts are made to monitor the efficiency of this process.

Step-4—Cell Separation and Cell Wash

Red blood cells are washed with six volumes of 0.9% sodium chloride. The process is carried out at 4±2° C. The cell wash is analyzed to verify removal of plasma components by a spectrophotometric assay for albumin.

Step-5—Red Blood Cell Lysis and Removal of Cell Debris

Washed red blood cells are lysed at least 4 hours or overnight at 4±2° C. with stirring using 6 volumes of water. Lysate is processed in the cold to purify hemoglobin. This is achieved by processing the lysate through a 0.16-$\mu$m membrane. Purified hemoglobin is collected in a sterile depyrogenated vessel. All steps in this process are carried out at 4±2° C.

Step-6—Viral Removal

Viral removal is performed by ultrafiltration at 4±2° C.

Step-7—Concentration and Solvent Exchange

Hemoglobin purified from lysate and ultrafiltration is exchanged into Ringer's lactate (RL) or phosphate-buffered saline (PBS, pH 7.4) using a 10-kD membrane. The hemoglobin is then concentrated using the same membrane to a final concentration of 1.1–1.5 mM (in tetramer). Ten to 12 volumes of RL or PBS are used for solvent exchange. This process is carried out at 4±2° C. The pH of the solution prepared in RL is adjusted to 7.0–7.6.

Step-8—Sterile Filtration

Hemoglobin in PBS or Ringer's lactate(RL) is sterile-filtered through a 0.45- or 0.2-$\mu$m disposable filter capsule and stored at 4±2° C. before the chemical modification reaction is performed.

Other methods for purifying hemoglobin are well known in the art. In addition, the use of a reducing agent (e.g., glutathione or another thiol-containing reducing agent) to prevent auto-oxidation after cell lysis is usually unnecessary.

Example 2

Modification of Stroma Free Hemoglobin

Step-1—Thiolation

Thiolation is carried out using 10-fold molar excess iminothiolane over hemoglobin for 4 hours at 4±2° C. with continuous stirring.

Reaction conditions:

1 mM hemoglobin (tetramer) in RL (pH 7.0–7.5) or PBS (pH 7.4)

10 mM iminothiolane in RL (pH 7.0–7.5) or PBS (pH 7.4)

The ratio of 1:10 SFH:iminothiolane and reaction timing were optimized to maximize the number of PEGylated thiol groups and to minimize product heterogeneity.

Step 2—PEGylation of Thiolated Hemoglobin

Thiolated hemoglobin is PEGylated using a 20-fold molar excess of Mal-PEG (with an alkyl or phenyl linker) based on starting tetrameric hemoglobin concentration. The hemoglobin is first allowed to equilibrate with the atmosphere to oxygenate the hemoglobin. The reaction takes place for 2 hours at 4±2° C. with continuous stirring.

Reaction conditions:

1 mM thiolated hemoglobin in RL or PBS (pH 7.4)

20 mM Mal-PEG in RL or PBS (pH 7.4)

Step 3—Removal of Unreacted Reagents

PEGylated-Hb is processed through a 70-kD membrane to remove excess unreacted reagents or hemoglobin. A 20-volume filtration is carried out to ensure removal of unreacted reagents, which is monitored by size-exclusion chromatography at 540 nm and 280 nm. The protein concentration is diluted to 4 g/dl. The pH is adjusted to 7.3±0.3 using 1 N NaOH.

Step-3—Sterile Filtration

The final MalPEG-Hb product is sterile-filtered using a 0.2-$\mu$m sterile disposable capsule and collected into a sterile depyrogenated vessel at 4±2° C.

Step-4—Formulation of MalPEG-Hb

PEGylated Hb is diluted to 4 g/dl RL, pH adjusted to 7.4±0.2

Step-5—Sterile Fill

The final blood substitute composition is sterile-filtered (0.2 $\mu$m) and aliquoted by weight into sterile glass vials and closed with sterile rubber stoppers with crimped seals in a laminar flow hood and stored at −80° C. until use.

Example 3

Physiochemical Analysis of MalPEG-Hb

Methodology for Physiochemical Analysis

Homogeneity and molecular size of the MalPEG-Hb blood substitute are characterized by Liquid Chromatography (LC). Analytical LC is used to evaluate homogeneity of the PEGylated hemoglobin and extent of removal of unreacted Mal-PEG. Absorbance at 540 nm is used to evaluate hemoglobin and resolves PEGylated hemoglobin from unreacted hemoglobin by peak position. Absorbance at 280 nm is used to resolve PEGylated hemoglobin from free Mal-PEG, which absorbs in the ultraviolet (UV) spectrum due to the ring structures in MalPEG.

Optical spectra are collected using a rapid scanning diode array spectrophotometer (Milton Roy 2000 or Hewlett Packard Model 8453) in the Soret and visible regions for analysis of hemoglobin concentration and percent methemoglobin by multicomponent analysis (Vandegriff, K. D., and R. E., Shrager. Evaluation of oxygen equilibrium binding to hemoglobin by rapid-scanning spcetrophotometry and singular value decomposition. Meth. Enzymol. 232: 460–485 (1994).

MalPEG-Hb concentration and percentage methemoglobin are determined using a co-oximeter. Viscosity is determined using a Rheometer. Colloid Osmotic Pressure is determined using a colloid osmometer. Oxygen binding parameters are determined from oxygen equilibrium curves.

The preferred specifications for the blood substitute composition are presented in Table 1 below:

TABLE 1

| Test | Specification |
|---|---|
| Hemoglobin concentration (g/dl) | 4.2 ± 0.2 |
| Methemoglobin (%) | <10 |
| pH | 7.4 ± 0.4 |
| Conductivity (mS/cm) | 12 ± 4 |
| Endotoxin (EU/mL) | <0.5 |
| FPLC retention time (min) | 43 ± 3 |
| FPLC peak width at half height (min) | 6 ± 2 |
| Viscosity (cPs) | 2.5 ± 1.0 |
| COP (mmHg) | 50 ± 20 |
| P50 (Torr) | 6 ± 2 |
| Hill number (at P50) | 1.2 ± 0.5 |
| Sterility | Pass |

Number of PEGylated Sites on MalPEG-Hb

For surface modification, the number "m" in Formula I is the parameter that defines the number of PEG polymers attached to the surface of hemoglobin.

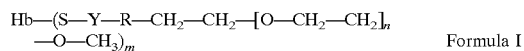

$$Hb\text{—}(S\text{—}Y\text{—}R\text{—}CH_2\text{—}CH_2\text{—}[O\text{—}CH_2\text{—}CH_2]_n\text{—}O\text{—}CH_3)_m \qquad \text{Formula I}$$

To determine this number, a dithiopyridine colorimetric assay (Ampulski, R., V. Ayers, and S. Morell. Determination of the reactive sulfhydryl groups in heme proteins with 4,4'-dipyridinesdisulde. Biocheim. Biophys. Acta 163–169, 1969) is used to measure the number of available thiol groups on the surface of the Hb tetramer before and after thiolation and then again after Hb PEGylation. Human hemoglobin contains 2 intrinsic reactive thiol groups at the β93Cys residues, which is confirmed by the dithiopyridine reaction. After thiolation of SFH at a ratio of 1:10 SFH: iminothiolane, the number of reactive thiol groups increases from 2 to 6 thiols based on the dithiopyridine reaction. After the PEGylation reaction, the number of reactive thiol groups is decreased to 1.3. This indicates that there are 4–5 PEGylated sites on MalPEG-Hb.

Size-Excluson Chromatography Analysis of MalPEG-Hb Versus SFH

FPLC is performed for analysis of the final MalPEG-Hb product. Typical chromatograms are displayed in FIG. 1 for MalPEG-Hb compared to unmodified SFH. The retention time for SFH is approximately 57 min. The retention time for MalPEG-Hb is approximately 44 min.

Physical and Chemical Characteristics of MalPEG-Hb

The physical properties of MalPEG-Hb compared to blood and unmodified human hemoglobin (SFH) are shown below in Table 2.

TABLE 2

| | Blood | SFH | MalPEG-Hb |
|---|---|---|---|
| P50 (Torr) | 28 | 15 | 5 |
| N50 (Hill number) | 2.9 | 2.9 | 1.2 |
| Bohr effect (ΔLog P50/ΔpH) | — | −0.46 | −0.20 |
| Viscosity (cPs)[1] | 4.0 | 0.9 | 2.5 |
| COP (mm Hg)[1] | 27 | 16 | 50 |
| MW (kD)[2] | N/A | 65 | 90 |
| Molecular Radius (nm) | 4000 | 3.2[2] | 9 |

Figure 2:
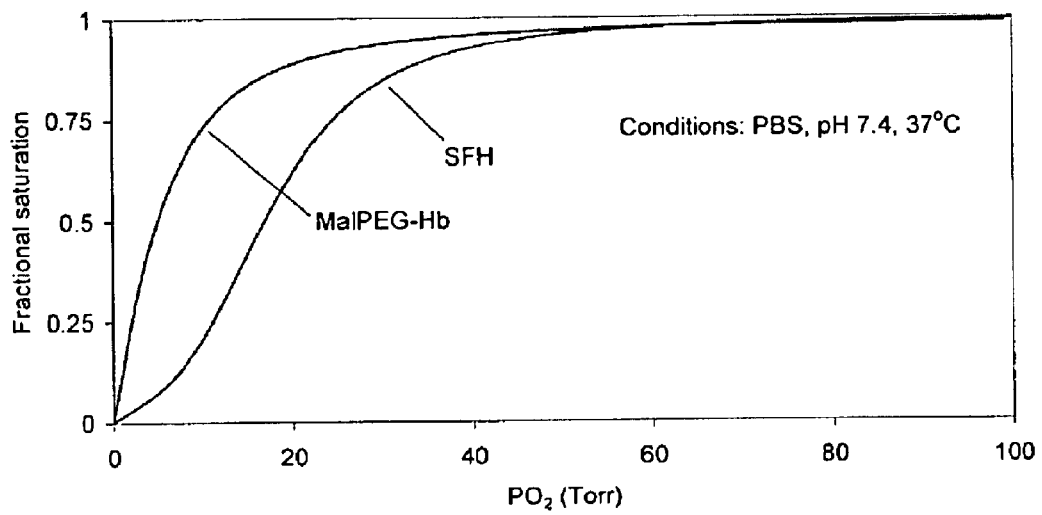
FIG. 2 depicts oxygen equilibrium curves for MalPEG-Hb and SFH.

[1]Determined at 15 g/dl for whole blood and approximately 4 g/dl for hemoglobin solutions
[2]Determined by COP measurements and FPLC Oxygen Affinity Hemoglobin-oxygen equilibrium binding curves were measured as described previously (Vandegriff, K. D., R. K. Rohlfs, M. D. Magde, and R M. Winslow. Hemoglobinoxygen equilibrium cures measured during enzymatic oxygen consumption. Anal. Biochem. 256: 107–116, 1998). MalPEG-Hb exhibits a high oxygen affinity (P50=5 mm Hg) and low cooperativity (n50=1.0–1.4). FIG. 2 shows representative curves comparing stroma-free hemoglobin (SFH) and MalPEG-Hb solutions.

Viscosity

This solution property of MalPEG-Hb is due to the strong interaction between polyethylene glycol chains and solvent water molecules. This is believed to be an important attribute for a blood substitute for two reasons: 1) higher viscosity decreases the diffusion constant of both the PEG-Hb molecule and gaseous ligand molecules diffusing through the solvent, and 2) higher viscosity increases the shear stress of the solution flowing against the endothelial wall, eliciting the release of vasodilators to counteract vasoconstriction. As shown in Table 2, the viscosity of the MalPEG-Hb solution is 2.5 cPs.

Colloidal Osmotic Pressure (COP)

The COP of hemoglobin solutions containing unmodified, intra- and intermolecularly cross-linked, or PEG-surface-conjugated hemoglobin have been measured to determine their macromolecular solution properties (Vandegriff, K. D., R. J. Rohlfs, and R. M. Wislow. Colloid osmotic effects of hemoglobin-based oxygen carriers. In Winslow, R. M., K. D. Vandegriff and M. Intaglia, eds, Advances in Blood Substitutes Industrial Opportunities and Medical Challenges. Boston, Birkhauser, pp. 207–232 (1997). Tetrameric hemoglobins show nearly ideal solution behavior; whereas hemoglobins conjugated to PEG have significantly higher colloid osmotic activity and exhibit solution non-ideality (Vandegriff, K. D., M. Mcarthy, R. J. Rohls and R. M. Winslow. Colloid osmotic properties of modified hemoglobins: chemically cross-linked versus polyethylene glycol surface-conjugated. Biophys. Chem. 69: 23–30 (1997). As shown in Table 2, the COP of the MalPEG-Hb solution is 50.

Stability

Figure 5:
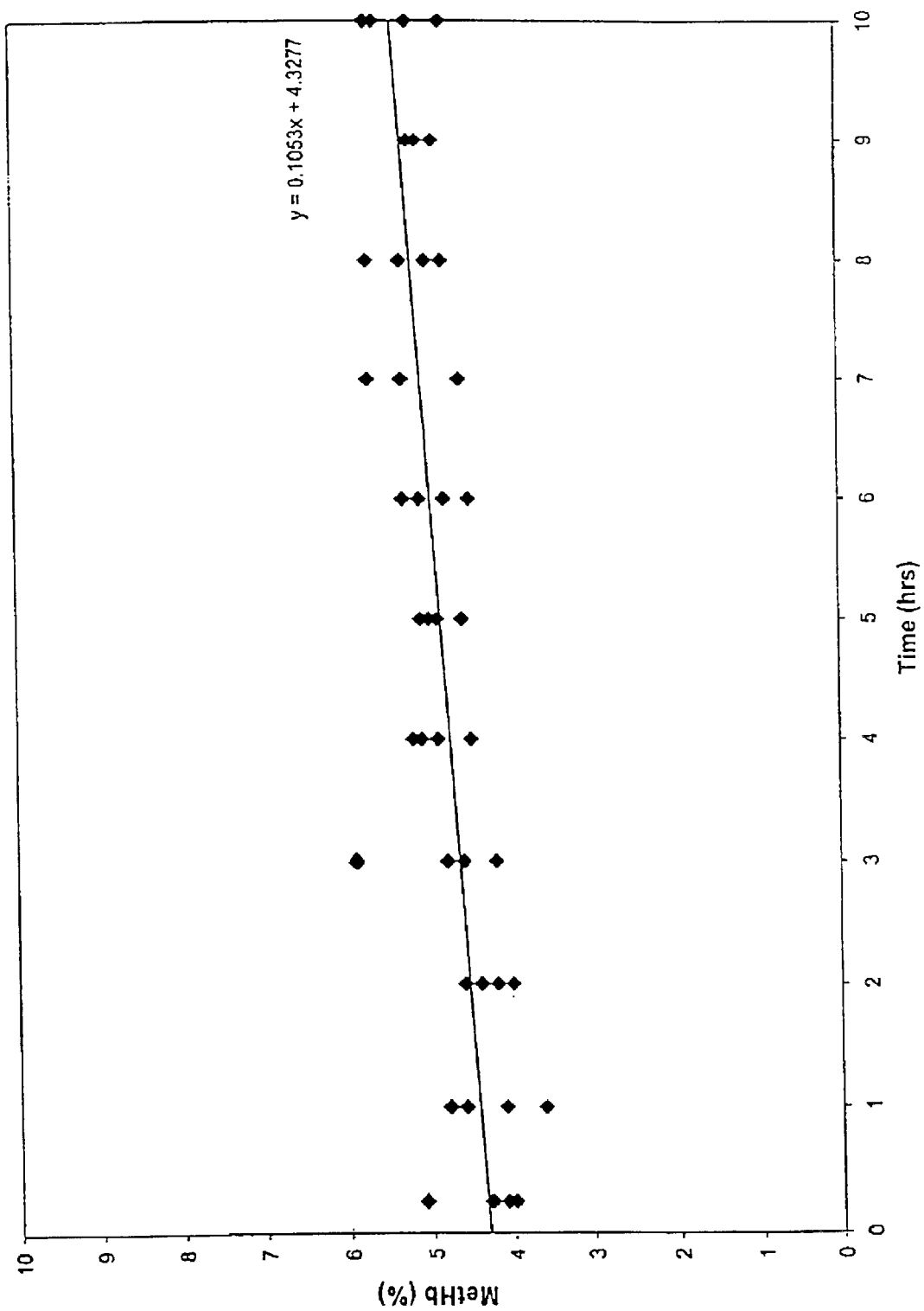
FIG. 5 depicts the rate of oxidation over time when MalPEG-hemoglobin is at room temperature. Samples were measured in duplicate from 2 separate bottles stored in the same way. The rate of oxidation is 1 percent per hour of total hemoglobin, going from 5.0 to 5.5 percent in 10 hours.

The stability of hemoglobin solutions containing PEG-surface-conjugated hemoglobin have been determined by examining the rate of autoxidation. At room temperature, the autoxidation of MalPEG-Hb increased from approximately 5% MetHb to 5.5% MetHb in 10 hours as shown in FIG. 5. The autoxidation rate for MalPEG-Hb was 0.05% per hour.

Example 4

Comparison of Modified Hemoglobins with Different P50s

The role of oxygen affinity in the efficacy of cell-free hemoglobin using hemoglobin modified by conjugation to polyoxyethylene (POE) is of particular interest in studying the efficacy of such materials as blood substitutes. This modification, first described by Iwashita and coworkers (Ajisaka, K. and Y. Iwashita, "Modification of human hemoglobin with polyethylene glycol: A new candidate for blood substitute. *BBRC* 97: 1076–1081 (1980)) (Iwasaki, K., K. Ajisaka, and Y. Iwashita, "Modification of human hemoglobin with polyoxyethylene glycol: A new candidate for blood substitutes," *Biochem Biophys Res Comm* 97: 1076–1981 (1980)), retains a hypertensive effect, and has been found to be useful in the treatment of septic shock. As part of the preparation of this product, hemoglobin was reacted with pyridoxal-5-phosphate (PLP) to raise its P50, close to the value for human blood. Thus it was possible to prepare two solutions of POE-modified hemoglobin, one with and one without prior modification with PLP. These solutions are identical in every way except for their P50, and were tested for their ability to support physiological function in rats during a severe (60% of blood volume) hemorrhage.

Materials and Methods
Blood Substitutes

The modified hemoglobin solutions, with or without PLP modification to form "PHP" were prepared as described above in Example 1.

Animals

Male Sprague-Dawley rats were used for this study. Systolic and diastolic pressures were monitored during the study; the maximum and minimum pressures, respectively, and the mean arterial pressure (MAP) was diastolic $+\frac{1}{3}$ (systolic-diastolic) pressure. The dP/dt was calculated from the maximum positive slope for each pressure cycle. Mean values of heart rate, systolic, diastolic, mean arterial pressures, pulse pressure and dP/dt were averaged for each minute of data.

Blood Gases, Hematologic, and Lactate Measurements

Arterial pH, $PCO_2$, and $PO_2$ were measured in a blood gas analyzer using 100 µl heparinized samples of blood. Lactic acid was measured in artery blood using a Lactate Analyzer. Total $CO_2$, standard bicarbonate ($HCO_3^-$), and base excess (BE) were calculated from $PCO_2$, pH and hemoglobin concentration using algorithms described previously (Winslow, R., "A model for red cell $O_2$ $_{uptake}$,". *Int J Clin Monit Comput* 2: 81–93 (1985)). Total hemoglobin and plasma hemoglobin were each measured using commercially available equipment. Hematocrit was measured using approximately 50 µl samples of arterial blood by microcentrifugation.

Exchange Transfusion

Exchange-transfusion was carried out at a rate of approximately 0.5 ml/min to a total volume of solution that equaled 50% of estimated blood volume. Blood volume was assumed to be 65 ml/kg. The peristaltic pump was operated so that blood was removed at exactly the same rate as test material was infused. Test solutions were warmed to 37° C. in a water bath prior to infusion and kept warm during infusion.

Hemorrhage

The hemorrhage protocol we used is based on the model of Hannon and Wade (Hannon, J., C. Wade, C. Bossone, M. Hunt, R. Coppes, and J. Loveday, "Blood gas and acid-base status of conscious pigs subjected to fixed-volume hemorrhage and resuscitated with hypertonic sali dextran," *Circ Shock* 32: 19–29 (1990)). Hemorrhage was begun approximately 3 minutes after completion of the exchange transfusion by pumping out arterial blood from the femoral artery at a rate of 0.5 ml/min to remove 60% of the blood volume by the end of 60 minutes. Blood samples (0.3 ml) were taken every 10 minutes for hematologic and blood gas analysis.

Statistical and Survival Analysis

For the survival analyses, animals were observed for a minimum of 120 minutes after the start of the hemorrhage. The data were grouped into 10-minute intervals, and for each interval the cumulative proportion alive and its standard error were calculated.

Results
Solution Properties

The solutions used are described below in Table 3. The total hemoglobin concentration, viscosity and colloid osmotic pressure (COP) are well-matched. The P50 of the PHP (19.7 Torr) was higher than that of the POE (12.2 Torr). The degree of cooperativity (Hill's parameter, n) were equivalent for the two solutions.

Figure 3:
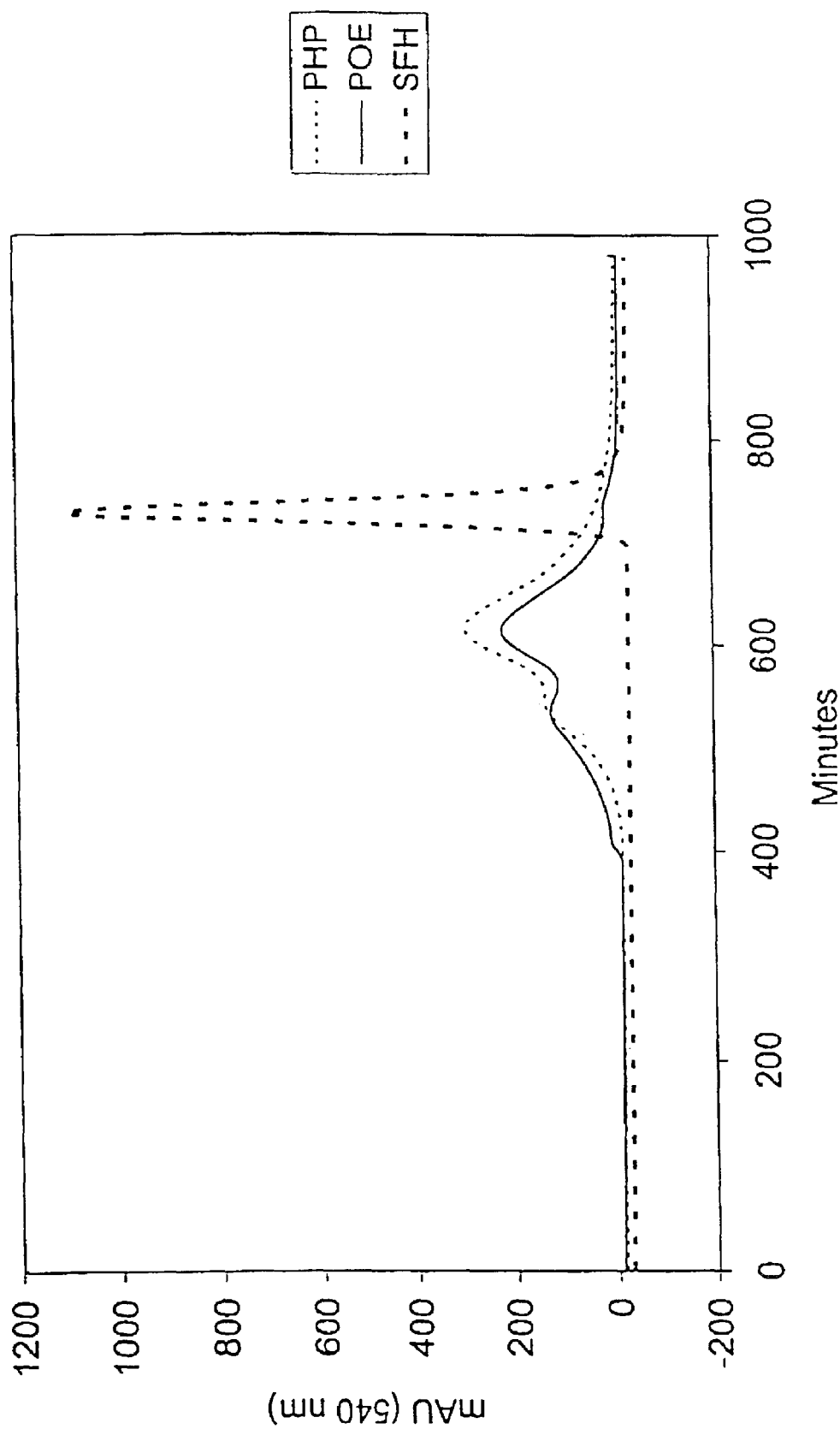
FIG. 3 depicts FPLC patterns of elution for the two PEG-modified hemoglobins (PHP and POE) and unmodified hemoglobin (SFH). Note that the patterns for PHP and POE are qualitatively, but not quantitatively, similar. Also, note the small peak of apparently unmodified hemoglobin in the POE curve.

The FPLC patterns for the two solutions are given in FIG. 3. While there is a small peak in each that corresponds to unmodified hemoglobin, the bulk of the hemoglobin appears in a heterogeneous set of peaks that elute significantly earlier than the unmodified hemoglobin (SFH). The patterns for the two PEG-modified hemoglobins are qualitatively similar.

TABLE 3

Table 1. Properties of the test solutions

|  | PHP | POE |
| --- | --- | --- |
| Hb, g/dl | 8.0 | 8.3 |
| Viscosity (cP) | 2.8 | 2.8 |
| COP, mm Hg | 62.7 | 56.5 |
| *$a_1$ (×10$^{-1}$) | 1.368 | 2.228 |
| *$a_2$ (×10$^{-3}$) | 9.680 | 21.070 |
| *$a_3$ (×10$^{-5}$) | 0.752 | 46.500 |
| *$a_4$ (×10$^{-5}$) | 1.537 | 8.766 |
| P50 | 19.7 | 12.2 |
| n50 | 1.48 | 1.49 |

*Oxygen Affinity Measured at 37° C., pH 7.4

Figure 4:
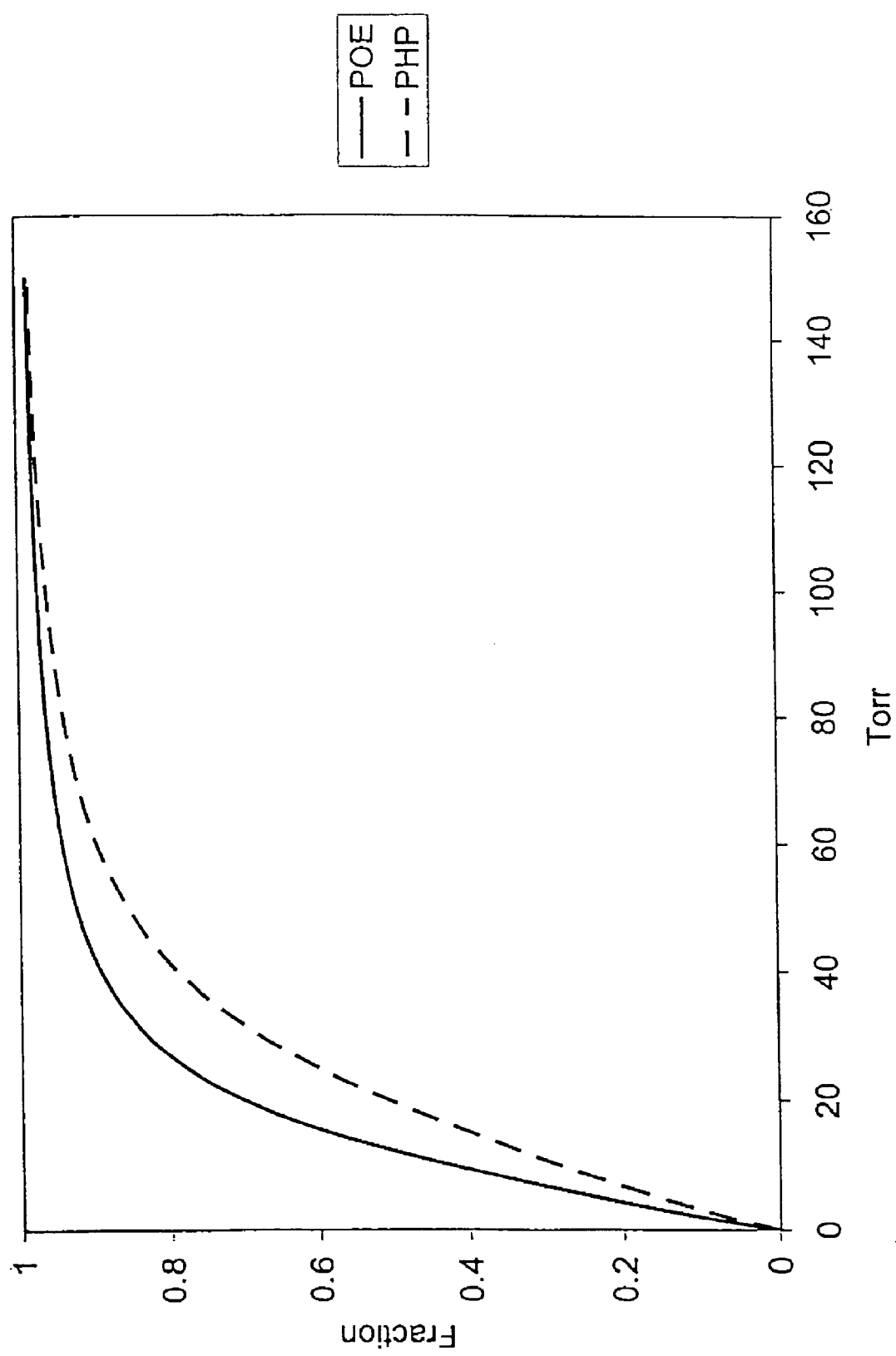
FIG. 4 depicts oxygen equilibrium curves for the two PEG-modified hemoglobins (PHP and POE). Note that neither has significant cooperativity.

The oxygen affinity of the POE was significantly higher than that of the PHP (FIG. 4). Neither product, however, displays significant cooperativity.

Animal Experiments

All experiments are summarized in Table 4. A larger number of animals received PHP (18) than POE (11), and the average weight of the PHP animals was significantly greater than that of the POE group (P<0.001). However, this difference in weight was accounted for in calculating the degree of hemorrhage, assuming a total blood volume of 65 ml/kg. Therefore the consequent volumes of exchange transfusion and hemorrhage were different as well. Nevertheless, the mean time to death was significantly shorter for the PHP animals (93 minutes) compared to the POE animals (116 minutes). This difference was statistically significant (P<0.02). If animals survived the observation period, 120 minutes after start of hemorrhage, they were considered "censored" for the purpose of the Kaplan-Meier survival analysis (FIG. 5).

TABLE 4

|  |  | WT (g) | *Blood Volume (ml) | Hemorrhage Volume (ml) | Hemorrhage Volume (%) | Time to Death (minutes) |
| --- | --- | --- | --- | --- | --- | --- |
| PHP | n | 18 | 18 | 18 | 18 | 18 |
|  | PHP | 291 | 18.89 | 11.10 | 58.79 | 93 |
|  | sd | 24 | 1.59 | 0.90 | 0.35 | 29 |
| POE | n | 11 | 11 | 11 | 11 | 11 |
|  | POE | 334 | 21.74 | 12.78 | 58.77 | 116 |
|  | sd | 41 | 2.65 | 1.60 | 0.39 | 12 |
|  | P | 0.001 | 0.001 | 0.001 | 0.915 | 0.020 |

*Based on 65 ml/kg total blood volume

Hematology and Acid-Base Regulation

The baseline, post-ET and post-hemorrhage (60 minute) measurements are shown in Table 5. The mean hematocrit was slightly higher in the POE compared to PHP animals, but after exchange transfusion the values were identical in the two groups. At the end of the hemorrhage period, the mean hematocrit in the POE animals was again slightly higher than in the PHP animals. Similar minor differences are found in the total hemoglobin values, with POE animals being slightly higher at all sampling points. Plasma hemoglobin was not different in the two groups, but was significantly higher in the POE animals after the exchange period.

Arterial lactic acid concentration was significantly higher in the POE compared to PHP animals at all stages of the study. The base excess values were not significantly different between the two groups, although there is a suggestion that the values are lower in the PHP compared to POE groups. Furthermore, the difference between baseline values for the PHP animals (10.24 mEq/l) is higher than for the POE animals (7.01 mEq/l).

TABLE 5

|  |  | n | PHP | sem | n | POE | sem | P |
|---|---|---|---|---|---|---|---|---|
| HCT | Baseline | 17 | 39.80 | 0.57 | 10 | 43.15 | 0.23 | 0.0032 |
|  | Post ET | 17 | 17.89 | 0.43 | 10 | 19.25 | 0.62 | 0.3568 |
|  | 60 minutes | 15 | 13.29 | 0.47 | 10 | 15.85 | 0.14 | 0.0015 |
| HB | Baseline | 17 | 13.59 | 0.22 | 10 | 15.08 | 0.17 | 0.0057 |
|  | Post ET | 17 | 8.70 | 0.18 | 10 | 9.74 | 0.07 | 0.0007 |
|  | 60 minutes | 15 | 6.34 | 0.21 | 10 | 7.38 | 0.06 | 0.0016 |
| PLHB | Baseline | 16 | 0.00 | 0.00 | 10 | 0.00 | 0.00 |  |
|  | Post ET | 16 | 2.86 | 0.07 | 10 | 2.99 | 0.09 | 0.6785 |
|  | 60 minutes | 15 | 1.93 | 0.07 | 10 | 2.47 | 0.02 | 0.0001 |
| LACT | Baseline | 9 | 0.70 | 0.06 | 7 | 2.68 | 0.16 | 0.0001 |
|  | Post ET | 9 | 1.59 | 0.10 | 7 | 4.21 | 0.24 | 0.0004 |
|  | 60 minutes | 9 | 10.62 | 0.89 | 7 | 17.27 | 1.18 | 0.0360 |
| BE | Baseline | 17 | 6.22 | 1.28 | 9 | 5.41 | 0.08 | 0.6530 |
|  | Post ET | 17 | 6.20 | 1.41 | 5 | 5.60 | 0.13 | 0.8101 |
|  | 60 minutes | 15 | −4.02 | 1.60 | 6 | −1.60 | 0.53 | 0.4678 |

Mean Arterial Pressure During Exchange Transfusion

Figure 6:
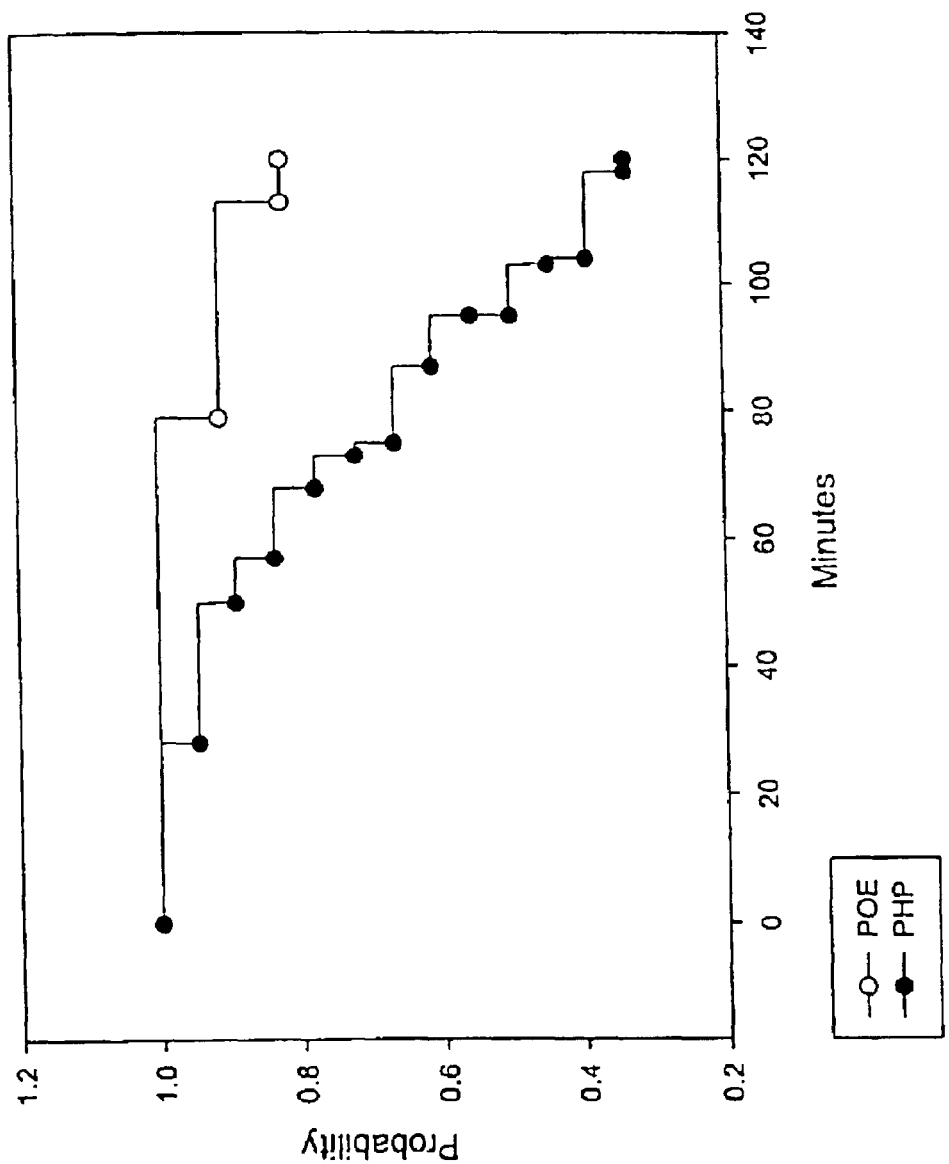
FIG. 6 depicts Kaplan-Meier survival analysis of the two groups of animals that received either PHP or POE.
Figure 7:
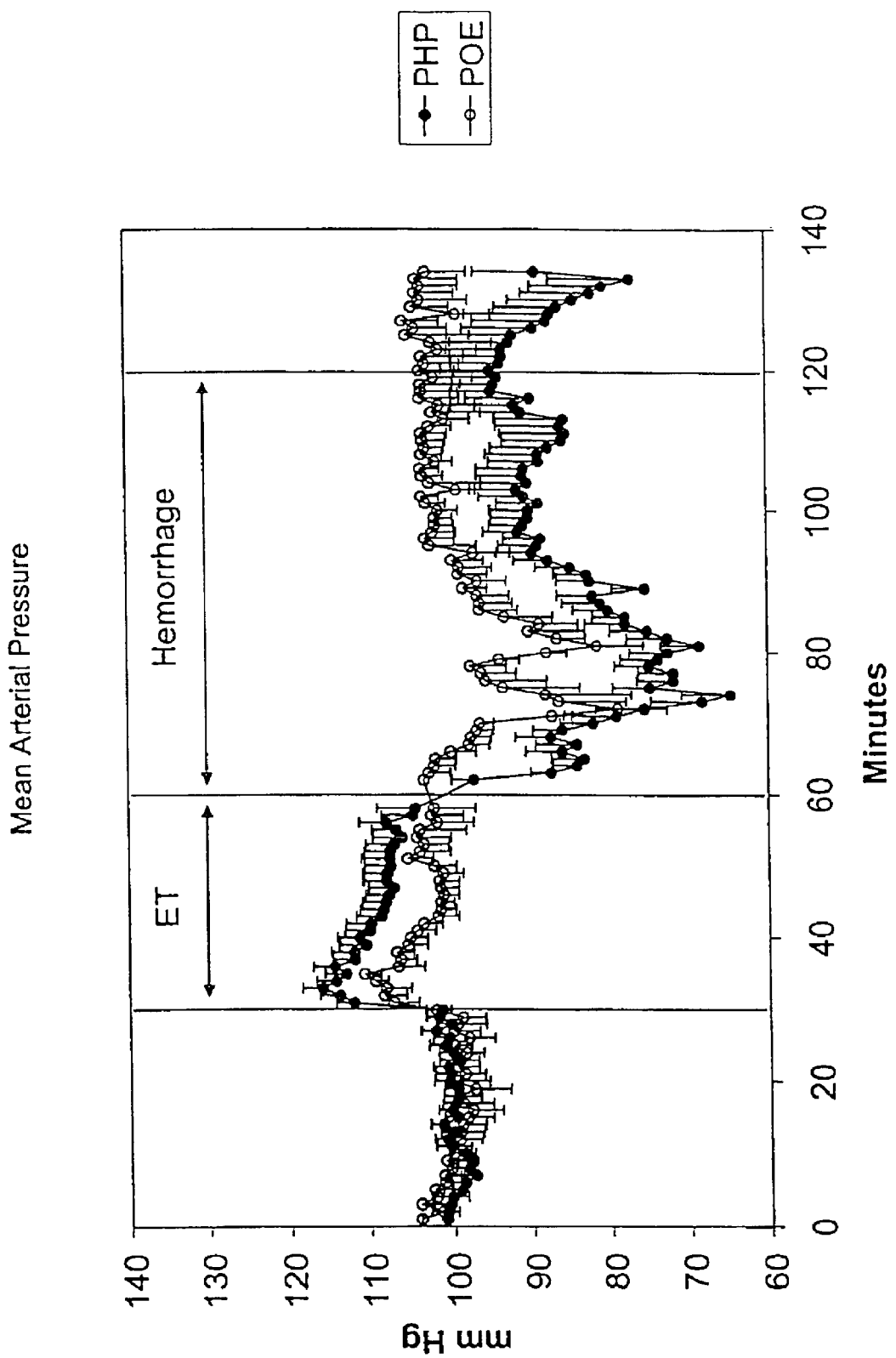
FIG. 7 depicts mean arterial pressure in animals that received the two PEG-modified hemoglobins (PHP and POE). The response is immediate and greater in the animals that received PHP. However, pressure is better maintained in the POE animals during the hemorrhage period.

The mean arterial pressure during exchange transfusion is shown in FIG. 6. Baseline mean arterial pressures are indistinguishable for the two groups. However, the blood pressure response to infusion of the PEG-hemoglobins is significantly different between the two groups. The initial rise in MAP is greater in the PHP compared to the POE animals, and it is sustained for the duration of the infusion period. In contrast, the MAP in the POE animals returns to baseline by the end of the infusion.

At the start of hemorrhage, the fall in MAP is immediate in the PHP animals and delayed in the POE group. Furthermore, the MAP is sustained at or near baseline values for the entire hemorrhage and beyond for the POE animals, while the MAP never returns to baseline values in the PHP animals. Especially in the PHP animals, the scatter in the data, as indicated by increasing standard errors, increases with time as animals drop out of the PHP group.

Discussion

In this study, we studied 2 closely matched modified hemoglobin solutions ("blood substitutes") with respect to their ability to protect rats from a severe (60% of blood volume) hemorrhage. In order to test this ability, animals first received a 50% (of blood volume) exchange transfusion with one of the two test solutions. The solutions themselves differed only in their oxygen affinity, and were matched very closely in FPLC pattern, oncotic pressure, viscosity and concentration. Other studies attempting to show the effects of specific variables on physiological outcomes have not been able to compare solutions as well matched. See.e.g., Sakai, H., Hara, H., Tsai, A. G., Tsuchida, E., Johnson, P. C., and Intaglietta, M., "Changes in resistance vessels during hemorrhagic shock and resuscitation in conscious hamster model," Am J.Physiol 276(45), H563–H571. (1999), Sakai, H., H. Hara, M. Yuasa, A. Tsai, S. Takeoka, E. Tsuchida, and M. Intaglietta, "Molecular dimensions of Hb-based $O_2$ carriers determine constriction of resistance arteries and hypertension," Am J Physiol 279: H908–H915, (2000). These experiments represent the first instance in which such closely matched solutions could be compared with only one variable, P50, being significantly different.

The group of animals that received POE had slightly, but significantly, higher hematocrits, total hemoglobins and plasma hemoglobin levels. However, it is very unlikely that these differences can explain the outcome or interpretation of the experiments. Clearly, the two solutions affect blood pressure in different ways, as shown in FIG. 4. At the time of infusion, the effect on blood pressure must be a function of the properties of the infused solution, not the recipient animals. The blood pressure response is greater and sustained in the PHP compared to POE animals.

Survival of the animals is clearly not linked to the pressor effect of the hemoglobin solutions, as has been suggested by some investigators in the past, because survival (and a suggestion of less base deficit) is better in the POE compared to PHP animals, in which the blood pressure effect is less and only transient. See Przybelski, R. J., E. K. Daily, and M. L. Birnbaum, "The pressor effect of hemoglobin—good or bad?" In Winslow, R. M., K. D. Vandegriff, and M. Intaglietta, eds. Advances in Blood Substitutes. Industrial Opportunities and Medical Challenges. Boston, Birkhäuser (1997), 71–85.

Taken together, these results support the hypothesis that a lower P50 is beneficial for the use of cell-free hemoglobin as an oxygen carrier. The hypothesis is based on 2 concepts. First, that the diffusion gradient for cell-free hemoglobin is a function of the oxyhemoglobin gradient between the source of oxygen, the red cell, and the vessel wall. This gradient, in turn is dependent on the shape and position of the oxygen equilibrium curve (McCarthy, M. R., K. D. Vandegriff, and R. M. Winslow, "The role of facilitated diffusion in oxygen transport by cell-free hemoglobin: Implications for the design of hemoglobin-based oxygen carriers," Biophysical Chemistry 92: 103–117 (2001)). Second, this consideration leads to the second conceptual basis of our hypothesis, that high oxygen affinity (low P50) effectively "hides" $O_2$ from the circulation until the carrier hemoglobin molecule arrives at regions of the circulation in which the $PO_2$ is very low, such as in ischemic or hypoxic tissue.

Example 5

Stability of MalPEG-Hb

The purpose of this study was to determine the stability of MalPEG-Hb during a simulation of the storage and handling conditions of the samples for Phase I clinical trials. The stability during three stages of handling were assessed. Stage I represented the transfer from frozen storage at the production facility to temperature conditions during shipping to the clinical site (frozen storage study). Stage II represented the thawing of the MalPEG-Hb for 24 hours to +4° C. and subsequent storage at +4° C. for five days (refrigerated study). Stage III represented the thawing of the MalPEG-Hb for 24 hours to +4° C. and subsequent storage of MalPEG-Hb at room temperature for several days prior to patient administration (room temperature study).

Experimental Methods

Stability was defined by the rate of oxidation of the MalPEG-Hb test material. The percentage of methemoglobin in the sample was measured using co-oximetry (IL Co-oximetry 682). Measurements were made in duplicate at each time point according to the protocol.

Temperatures were monitored by thermometer or temperature chart recorders. The frozen storage study was conducted over a temperature range of −21.0±3.0° C. The refrigerated study was conducted over a temperature range of +4.0±0.2° C. The room temperature study was conducted over a temperature range of +21.0±1.0° C.

Temperature, total hemoglobin, and percent methemoglobin were recorded at each of the indicated time points. In the frozen and refrigerated studies, measurements were taken at time zero (completely thawed), one hour later, and then every 24 hours for five days. In the room temperature study, measurements were taken at time zero (completely thawed) and subsequently every one hour for ten hours.

Results

Figure 8:
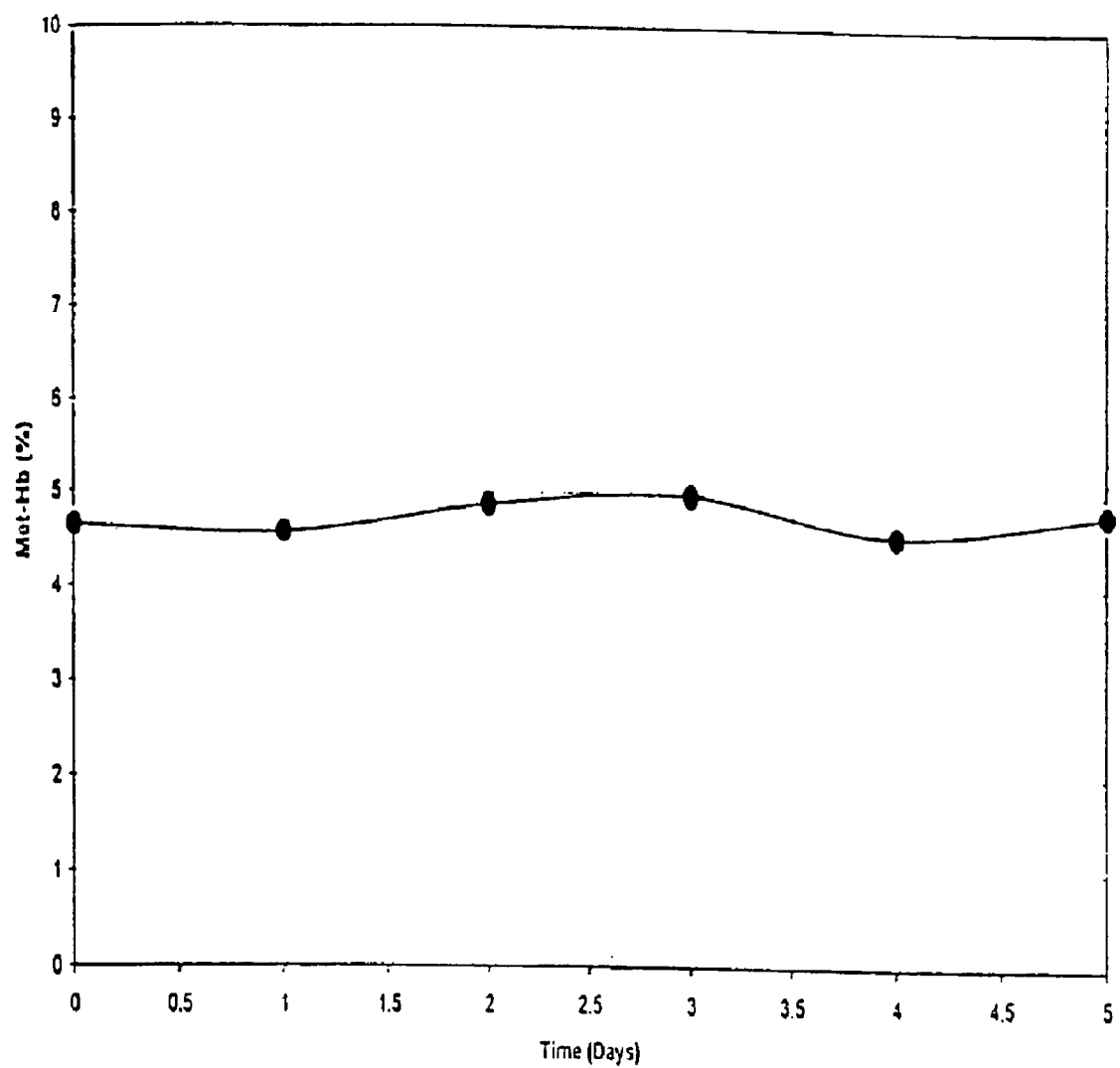
FIG. 8 depicts a summary of various rates of oxidation over time when MalPEG-Hb is stored for six days at −20° C., five days at +4° C., and ten hours at room temperature (24° C.).
Figure 9:
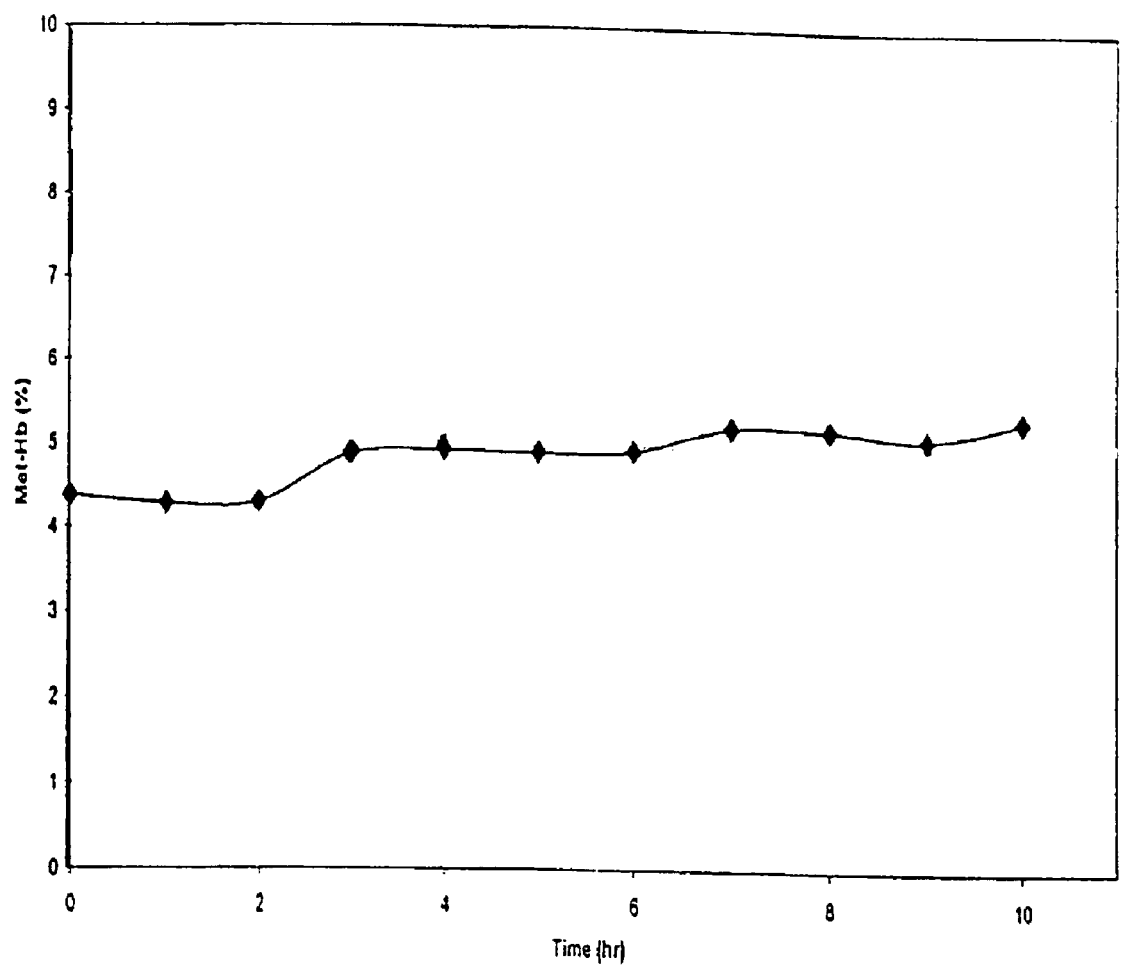
FIG. 9 depicts the rate of oxidation over time when MalPEG-Hb is stored for five days at +4° C.
Figure 10:
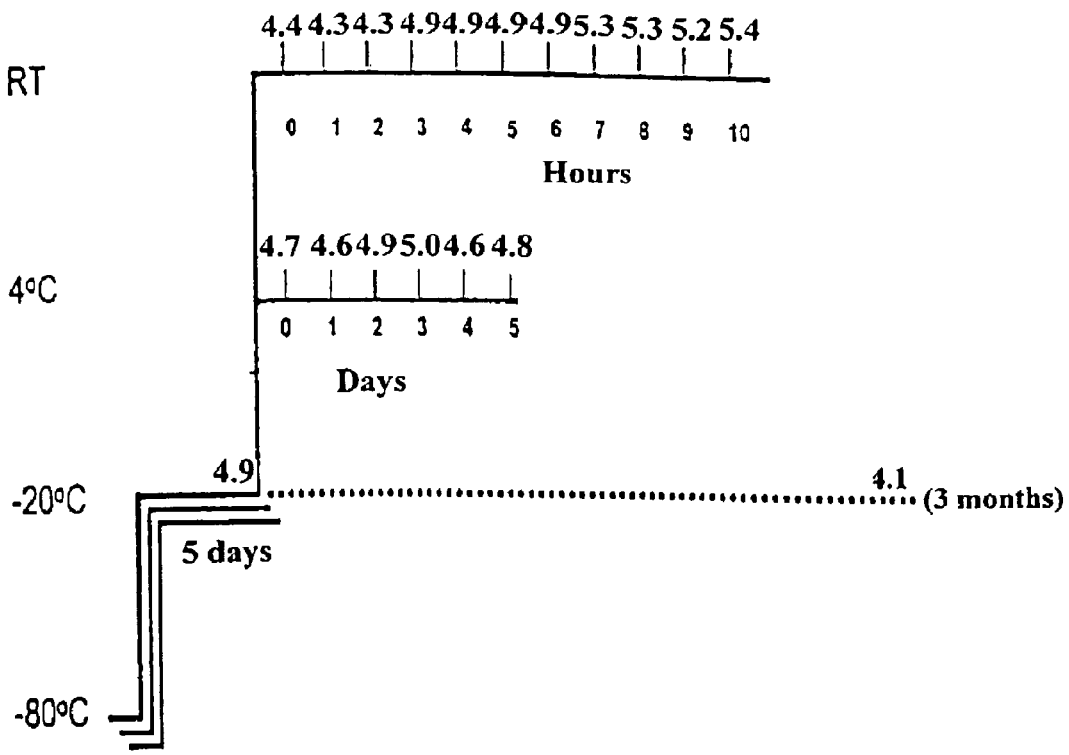
FIG. 10 depicts the rate of oxidation over time when MalPEG-Hb is stored for ten hours at room temperature.

MalPEG-Hb showed no change in percent methemoglobin during 6 day storage at −20° C. as shown in FIG. 8. Similarly, MalPEG-Hb showed no change in percent methemoglobin during five day storage at +4° C. as shown in FIG. 9. During storage at room temperature, MalPEG-Hb showed less than 1 percent increase in methemoglobin over a ten hour period as shown in FIG. 10.

The examples set forth above are provided to give those of ordinary skill in the art with a complete disclosure and description of how to make and use the preferred embodiments of the compositions, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

We claim:

1. A method of using a blood substitute product to deliver oxygen to a tissue, comprising administering to a mammal in need thereof a composition comprising:

a) a blood substitute product adapted for delivery of oxygen to tissues comprising polyalkylene oxide (PAO) modified oxygenated hemoglobin, wherein the PAO modified oxygenated hemoglobin has a P50 less than native stroma-free hemoglobin from the same animal source when measured under the same conditions, and wherein the PAO modified oxygenated hemoglobin is stable to autooxidation and has a methemoglobin/total hemoglobin ratio of less than 0.1; and b) an aqueous diluent.

2. The method of claim 1 wherein the PAO modified oxygenated hemoglobin has a P50 less than 10 Torr.

3. The method of claim 1, wherein the PAO modified oxygenated hemoglobin has a P50 of 6+/−2 torr.

4. The method of claim 1, wherein the PAO is polyethylene glycol (PEG) according to the formula of $H(OCH_2CH_2)_nOH$, where n is greater than or equal to 4.

5. The method of claim 1, wherein the composition further comprises proteins, glycoproteins, and polysaccharides.

6. The method of claim 1, wherein the blood substitute product is adapted for delivery of oxygen to tissues comprising oxygenated hemoglobin conjugated with malemidyl-activated polyethylene glycol (Mal-PEG), and having the formula:

$$Hb-(S-Y-R-CH_2-CH_2[O-CH_2-CH_2]_nO-CH_3)_m$$

wherein:
Hb is tetrameric hemoglobin;
S is a surface thiol group;
Y is a covalent bond between hemoglobin and PEG;
R is a linker; and
m is greater than 2.

7. The method of claim 6, wherein m is 4–5.

8. The method of claim 6, wherein R is $C_1$ to $C_6$ aliphatic alkyl.

9. The method of claim 7, wherein the $C_1$ to $C_6$ aliphatic alkyl is methyl.

10. The method of claim 1, wherein the concentration of hemoglobin is between 0.1 to 4.0 g/dl.

11. The method of claim 1, wherein the viscosity is 2.5+/−1.0 cPs.

12. The method of claim 1, wherein the PAO modified oxygenated hemoglobin has a P50 less than 6 torr.

13. The method of claim 1, wherein the PAO is attached to surface thiol groups on the hemoglobin.

14. The method of claim 13, wherein at least some of the surface thiol groups are chemically added to the hemoglobin prior to attachment.

15. The method of claim 1, wherein the PAO is attached to the hemoglobin with a linker.

16. The method of claim 15, wherein the linker is an alkyl, amide, carbamate or phenyl group.

17. The method of claim 16, wherein the linker is an unsaturated aliphatic or aromatic $C_1$ to $C_6$ moiety.

18. The method of claim 1, wherein the hemoglobin further comprises methemoglobin.

19. The method of claim 18, wherein the percent methemoglobin is less than 10%.

20. The method of claim 1, wherein the PAO modified oxygenated hemoglobin is exposed to aerobic conditions for a time sufficient to lower the methemoglobin/total hemoglobin ratio to less than 0.10.

21. The method of claim 1, wherein the mammal has symptoms of sickle cell anemia.

22. The method of claim 1, wherein the mammal has symptoms of hematopoiesis.

23. The method of claim 1, wherein the mammal has cancer.

24. The method of claim 1, wherein the mammal is a non-human.

25. The method of claim 1, wherein the PAO modified oxygenated hemoglobin is from horse.

26. The method of claim 1, wherein the mammal is a dog, cat, horse, bird or reptile.

27. The method of claim 1, wherein the mammal is housed in an aquarium, zoo or oceanarium.

28. The method of claim 1, wherein the mammal is suffering a loss of blood due to injury.

29. The method of claim 1, wherein the mammal is suffering from hemolytic anemia.

30. The method of claim 1, wherein the mammal is suffering from equine infectious anemia.

31. The method of claim 1, wherein the mammal is suffering from feline infectious anemia.

32. The method of claim 1, wherein the mammal is suffering from bacterial infection.

33. The method of claim 1, wherein the mammal is suffering from Factor IV fragmentation.

34. The method of claim 1, wherein the mammal is suffering from hypersplenation.

35. The method of claim 1, wherein the mammal is suffering from splenomegaly.

36. The method of claim 1, wherein the mammal is poultry and is suffering from hemorrhagic syndrome.

37. The method of claim 1, wherein the mammal is suffering from hypoplastic anemia.

38. The method of claim 1, wherein the mammal is suffering from aplastic anemia.

39. The method of claim 1, wherein the mammal is suffering from idiopathic immune hemadytic conditions.

40. The method of claim 1, wherein the mammal is suffering from iron deficiency.

41. The method of claim 1, wherein the mammal is suffering from isoimmune hemdytic anemia.

42. The method of claim 1, wherein the mammal is suffering from microangiopathic hemolytic anemia.

43. The method of claim 1, wherein the mammal is suffering from parasitism.

* * * * *